United States Patent
Zhang et al.

(10) Patent No.: US 10,982,213 B2
(45) Date of Patent: Apr. 20, 2021

(54) K-RAS GENE EXPRESSION-SUPPRESSING SIRNA, PRECURSOR OF SAME, AND APPLICATIONS THEREOF

(71) Applicant: JIANGSU MICROMEDMARK BIOTECH CO., LTD., Jiangsu (CN)

(72) Inventors: Chenyu Zhang, Jiangsu (CN); Xi Chen, Jiangsu (CN); Hongwei Liang, Jiangsu (CN); Uzair Ur-Rehman, Jiangsu (CN); Ke Zeng, Jiangsu (CN)

(73) Assignee: JIANGSU MICROMEDMARK BIOTECH CO., LTD., Jiangsu (CN)

( * ) Notice: Subject to any disclaimer, the term of this patent is extended or adjusted under 35 U.S.C. 154(b) by 0 days.

(21) Appl. No.: 16/098,960

(22) PCT Filed: May 5, 2017

(86) PCT No.: PCT/CN2017/083311
§ 371 (c)(1),
(2) Date: May 6, 2019

(87) PCT Pub. No.: WO2017/190694
PCT Pub. Date: Nov. 9, 2017

(65) Prior Publication Data
US 2019/0382769 A1 Dec. 19, 2019

(30) Foreign Application Priority Data
May 5, 2016 (CN) .......................... 201610292198.4

(51) Int. Cl.
*C12N 15/113* (2010.01)
*A61K 31/7088* (2006.01)

(52) U.S. Cl.
CPC ...... *C12N 15/1137* (2013.01); *A61K 31/7088* (2013.01); *C12N 2310/141* (2013.01); *C12N 2320/30* (2013.01)

(58) Field of Classification Search
CPC .............. C12N 15/111; C12N 2310/14; C12N 2310/533; C12N 15/113; C12N 2310/531; C12N 2320/30; A61P 35/00
USPC ...................... 435/6.1, 91.1, 91.31, 455, 458; 514/44 A; 536/23.1, 24.5
See application file for complete search history.

(56) References Cited

U.S. PATENT DOCUMENTS

| 8,008,474 B2 | 8/2011 | Khvorova et al. |
| 2013/0011922 A1* | 1/2013 | Quay .................... C12N 15/111 |
| | | 435/366 |
| 2018/0223277 A1 | 8/2018 | Zhang et al. |

FOREIGN PATENT DOCUMENTS

| WO | 2016/177343 A1 | 11/2016 | |
| WO | WO-2016177343 A1 * | 11/2016 | ........... A61K 31/713 |

OTHER PUBLICATIONS

International Search Report dated Aug. 14, 2017 issued in corresponding PCT/CN2017/083311 application (6 pages).
F. Meng, "Inhibition of K-RAS ASN12 Expression by Vector-Based RNA Interference in Human Pancreatic Cancer Cell Line", China Biotechnology, vol. 26, No. 4 (2006) pp. 86-90.

* cited by examiner

*Primary Examiner* — Jane J Zara
(74) *Attorney, Agent, or Firm* — Millen White Zelano and Branigan, PC; Csaba Henter

(57) ABSTRACT

The present invention discloses an siRNA that inhibits K-RAS gene expression, and the precursor sequences and applications thereof. The K-RAS siRNA and its precursor sequences provided by the present invention can efficiently inhibit the expression of the K-RAS gene, and in vivo experiments have shown that the K-RAS siRNA has a certain inhibitory effect on tumours highly expressing K-RAS. The precursor of the siRNA of the invention and its vector can form a stable siRNA that functions in a host.

20 Claims, 7 Drawing Sheets

Specification includes a Sequence Listing.

K-RAS GENE EXPRESSION-SUPPRESSING SIRNA, PRECURSOR OF SAME, AND APPLICATIONS THEREOF

TECHNICAL FIELD

The present invention belongs to the biomedical field, and specifically pertains to a siRNA which inhibits the K-RAS gene expression, and the precursors and applications thereof.

BACKGROUND ART

RNA interfering (RNAi) is a powerful experimental tool in the laboratory, using double-stranded RNA (dsRNA) having homology to induce the sequence-specific silencing of a target gene, thereby rapidly blocking its activity. The siRNA plays a central role in the RNA silencing pathway and is a guiding element for the degradation of a specific messenger RNA (mRNA). siRNA is an intermediate product in the RNAi pathway and is an essential factor for RNAi to exert effects. The formation of siRNA is mainly regulated by Dicer and Rde-1. Due to RNA virus invasion, transposon transcription, reverse repeat sequence transcription in the genome and other factors, dsRNAs appear in the cell, and the protein encoded by Rde-1 (RNAi deficient gene-1) recognizes the foreign dsRNA. When the level of dsRNA reaches a certain amount, Rde-1 guides the dsRNA to bind to Rde-1 encoded Dicer (Dicer is an RNaseIII active endonuclease with four domains: PAZ domain of the Argonaute family, type III RNase active region, a dsRNA binding region and a DEAH/DEXHRNA helicase active region), forming an enzyme-dsRNA complex. The siRNA forms after cleavage by Dicer, and then, with the participation of ATP, a RNA-induced silencing complex (RISC) is formed in the cell. A key step in RNAi is to assembly RISC and synthesize siRNA protein mediating specific reaction. siRNA is incorporated into RISC and then degrades a target gene by fully pairing with the coding region or a UTR of it, thus saying that a siRNA only degrades the mRNA that is in complementary pair with the sequence of the siRNA. The mechanism of its regulation is to silence the expression of the corresponding target gene through complementary pairing, and is thus a typical negative regulation mechanism. The siRNA recognition of the target sequence is highly specific, since degradation occurs first in a relatively central position of the siRNA, and therefore these central base sites are extremely important and the effect of RNAi can be severely inhibited in the event of a mismatch. As an emerging therapeutic technology, siRNA has also entered the clinical trial stage at an unprecedented rate.

K-RAS is one member of the RAS gene family, encoding the K-RAS protein. It is related to the formation, proliferation, migration, metastasis and angiogenesis of tumour.

K-RAS protein has GTPase activity, which is in an activated state when it is bound with GTP and in an inactivated state when it is bound with GDP. The K-RAS protein mainly localizes itself on the cell membrane. After the K-RAS protein is phosphorylated by PKC, this phosphorylation process causes the localization change of K-RAS protein due to the weakening of the binding of K-RAS protein to the cell membrane, and then movement to positions such as the endoplasmic reticulum, Golgi apparatus and mitochondria, and etc. The K-RAS protein serves as a molecular switch and plays an important role in many signalling pathways.

Research has shown that about 30% of human malignancies are associated with RAS gene mutations, and products of mutated RAS can remain in an activated state. K-RAS mutations are common in leukaemia, lung cancer, rectal cancer and pancreatic cancer, with 30%-35% of patients with rectal cancer having the mutations. They are associated with the survival, proliferation, migration, metastasis and angiogenesis of tumour cells. K-RAS genes are divided into mutant types and wild type, and the common mutation sites are codons 12 and 13 on the K-RAS gene exon 2, and codon 61 of the exon 3, wherein there are 7 mutation hotspots: G12C, G12R, G12S, G12V, G12D, G12A, and G13V/D. These 7 types account for 90% or more of the mutations.

The current EGFR targeted drugs on the market are mainly: Gefitinib (Iressa), erlotinib (Tarceva), Cetuximab (ERBITUX), panitumumab (Vectibix). However, EGFR targeted drugs are very ineffective for patients with K-RAS mutations, because even though there is no EGFR signal, K-RAS is still in an activated state to transmit signals downstream, so in personalized medication it is necessary to detect the K-RAS gene state and then select the drug. If K-RAS is of a mutant type, it is not recommended to use EGFR targeted drugs.

Therefore, considering that if the EGFR and K-RAS pathways can be targeted at the same time, then the upstream and downstream of the pathway can be simultaneously inhibited, thereby producing a better therapeutic effect by the EGFR targeted drug on patients with K-RAS mutations. Therefore, there is an urgent need for a treatment method and corresponding drugs that can targetedly inhibit of the K-RAS gene to solve the current problems such as the absence of drugs specific for the K-RAS mutation, and E'GFR targeted drugs are ineffective due to the K-RAS mutation.

SUMMARY OF THE INVENTION

The present invention provides a novel siRNA that inhibits the K-RAS gene, and precursors and applications thereof in the treatment of tumours.

The first aspect of the invention provides a precursor sequence, characterised in that it has a structure from the 5' terminus to the 3' terminus as shown in formula I:

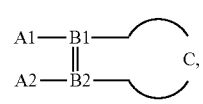

Formula I wherein B1 is a first ribonucleic acid sequence as desired, comprising a K-RAS siRNA sense strand sequence;

B2 is a sequence with substantial or complete complementarity to B1, and B2 is not complementary to C;

C is a stem-loop structure sequence, preferably GUUUUGGCCACUGACUGAC;

A1 and A2 are null, or are optionally RNA sequences consisting of 4-5 bases, respectively;

wherein the nucleotide sequence of the K-RAS siRNA sense strand is selected from the following sequences as shown in the sequence listing: SEQ ID NO: 3, SEQ ID NO: 26, SEQ ID NO: 41, SEQ ID NO: 47, SEQ ID NO: 52, SEQ ID NO: 73, SEQ ID NO: 88, SEQ ID NO: 98, SEQ ID NO: 101, and SEQ ID NO: 106 or SEQ ID NO: 263;

In another preferred example, there are 2-8, preferably 3-5 non-complementary bases between the B2 and B1.

In another preferred example, 1-2 bases are added or deleted in the B2 as compared with the B1.

In another preferred example, 1-2 bases, preferably 2 bases, are deleted in the B2 as compared with the B1.

In another preferred example, the said deleted 1-2 bases are in the middle of B1, i.e., 1-2 bases at positions 9-14, such as positions 9-10, 10-11, 11-12, 12-13 or 13-14.

In another preferred example, the A1 is UGCUG; and/or the A2 is CAGG or CAGGA.

In another preferred example, A2 is preferably CAGG.

The second aspect of the present invention provides a polynucleotide, which can be transcribed by a host to form the precursor sequence of the first aspect of the present invention.

The third aspect of the present invention provides an expression vector containing the precursor sequence of the first aspect of the present invention, or the polynucleotide of the second aspect of the present invention.

In another preferred example, the expression vector comprises a viral vector and a non-viral vector.

In another preferred example, the expression vector is a plasmid.

In another preferred example, the upstream of the polynucleotide of the second aspect of the present invention is a promoter, and the downstream thereof is a TKPA element.

The fourth aspect of the present invention provides a pharmaceutical preparation comprising:

(a) an expression vector for expression of a K-RAS siRNA sequence; and (b) a pharmaceutically acceptable carrier. In another preferred example, the K-RAS siRNA sequence is selected from the sequences group: SEQ ID NO: 3, SEQ ID NO: 26, SEQ ID NO: 41, SEQ ID NO: 47, SEQ ID NO: 52, SEQ ID NO: 73, SEQ ID NO: 88, SEQ ID NO: 98, SEQ ID NO: 101, and SEQ ID NO: 106 or SEQ ID NO: 263.

In another preferred example, the said expression vector expresses the precursor as shown in formula I,

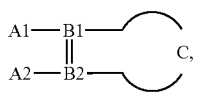

Formula I

Wherein, B1 is a first ribonucleic acid sequence as desired, comprising a K-RAS siRNA sense strand sequence;

B2 is a sequence with substantial or complete complementarity to B1, and B2 is not complementary to C;

C is a stem-loop structure sequence; and

A1 and A2 are null, or are optionally RNA sequences consisting of 4-5 bases, respectively;

In another preferred example, the first ribonucleic acid sequence is a K-RAS siRNA sense strand, and the second ribonucleic acid sequence is a K-RAS siRNA antisense strand.

In another preferred example, the preparation is in a liquid dosage form.

In another preferred example, the preparation is an injection.

In another preferred example, the expression vector comprises a plasmid.

In another preferred example, the expression vector or plasmid contains a promoter, an origin of replication and a marker gene.

In another preferred example, the expression vector contains an expression cassette expressing the K-RAS siRNA.

In another preferred example, the expression cassette (i.e., a polynucleotide) is double-stranded, and has the following structure:

a promoter-attB1—an optional tag protein (such as GFP or emGFP)—a 5' siRNA flanking region sequence—the sequence as shown in formula I—a 5' siRNA flanking region sequence-attB2—an optional TKPA element.

In another preferred example, the preparation is a liposome preparation.

The fifth aspect of the present invention provides a method for administering a medicament, comprising the step of:

administering the pharmaceutical preparation of the fourth aspect of the present invention at a first site of a mammal, so that the expression vector is processed to form microvesicles in the mammal, which are transported to a second site on the mammal where the siRNA is expressed.

In another preferred example, the said mammal comprises human and non-human mammals.

In another preferred example, the said first site comprises a subcutaneous, intravenous or gastrointestinal tract site.

In another preferred example, the said second site comprises liver, lung, and kidney.

In another preferred example, the said administering comprises oral intake, subcutaneous injection, intramuscular injection and intravenous injection.

The sixth aspect of the invention provides an siRNA for inhibiting K-RAS gene expression, wherein the nucleotide sequence of the siRNA sense strand is selected from the following sequences as shown in the sequence listing: SEQ ID NO: 3, SEQ ID NO: 26, SEQ ID NO: 41, SEQ ID NO: 47, SEQ ID NO: 52, SEQ ID NO: 73, SEQ ID NO: 88, SEQ ID NO: 98, SEQ ID NO: 101, and SEQ ID NO: 106 or SEQ ID NO: 263.

In another preferred example, the said nucleotide sequence of the siRNA sense strand is shows as SEQ ID NO: 263 in the sequence listing.

The seventh aspect of the present invention provides a pharmaceutical composition comprising the precursor sequence of the first aspect of the present invention, the expression vector of the third aspect of the present invention, or the siRNA of the sixth aspect of the present invention, and a pharmaceutically acceptable carrier.

In another preferred example, the pharmaceutical composition includes the K-RAS siRNA plasmid.

In another preferred example, the pharmaceutical composition also includes EGFR targeted drugs.

In another preferred example, the pharmaceutical composition is the expression vector of the third aspect of the present invention, and preferably is a plasmid containing the precursor sequence of the first aspect of the present invention.

In another preferred example, the dosage form of the pharmaceutical composition comprises:

a tablet, a capsule, a powder, a pill, a granule, a syrup, a solution, a suspension liquid, an emulsion, a suspension, an injection solution, or an injectable powder.

In another preferred example, the dosage form of the pharmaceutical composition further comprises a spray, an aerosol, a powder spray, a volatile liquid, a topical solution, a lotion, a pour-on agent, a liniment, a cataplasma, a medicinal paste, a rubber paste, an ointment, a plaster, a paste, an eye drop, a nasal drop, an ophthalmic ointment, a mouth wash, a sublingual tablet, or a suppository.

In another preferred example, the dosage form is an injection, preferably an intravenous injection or an intraperitoneal injection.

The eighth aspect of the present invention provides the use of the siRNA of the first aspect of the present invention, of the precursor sequence of the first aspect of the present invention or of the expression vector of the third aspect of the present invention, comprising the use: (i) for preparing an inhibitor of K-RAS; and/or (ii) for preparing a pharmaceutical composition against a malignant tumour highly expressing K-RAS.

In another preferred example, the malignant tumour comprises kidney cancer, oral epithelial cancer, head and neck cancer, bladder cancer, brain tumour, glioblastoma, liver cancer, lung cancer, stomach cancer, oesophageal cancer, ovarian cancer, colon cancer, rectal cancer, cervical cancer, pancreatic cancer, prostatic cancer, leukaemia or breast cancer.

The ninth aspect of the present invention provides a method for inhibiting the growth of malignant tumour cells highly expressing K-RAS in a non-therapeutic manner in vitro, comprising the steps of:

culturing the malignant tumour cells highly expressing K-RAS in the presence of the pharmaceutical composition of the seventh aspect of the present invention, so as to inhibit the growth of malignant tumour cells highly expressing K-RAS.

The tenth aspect of the present invention provides a method for treating malignant tumour highly expressing K-RAS, which involves administering a safe and effective amount of the expression vector of the third aspect of the present invention, or the pharmaceutical composition of the seventh aspect of the present invention, to a subject in need, so as to treat diseases associated with highly expressed K-RAS.

In another preferred example, the administered dosage is 0.05-10 mg/kg, preferably 0.1-5 mg/kg.

In another preferred example, the administering comprises oral, respiratory tract, injection, transdermal, mucosal, or cavity administration.

In another preferred example, the administering comprises plasmid injection.

The eleventh aspect of the present invention provides a method for treating diseases associated with highly expressed K-RAS, characterized in that the method involves administering the K-RAS siRNA plasmid containing the precursor sequence of the first aspect of the present invention by intravenous injection to a subject in need, so as to treat the diseases associated with highly expressed K-RAS.

It should be understood that all of the various technical features described above and specifically described hereinafter (such as the examples) can be combined with one another within the scope of the present invention, so as to form new or preferred technical solutions. Due to space limitations, these are no longer tired out one by one.

DETAILED DESCRIPTION OF EMBODIMENTS

Figure 1:
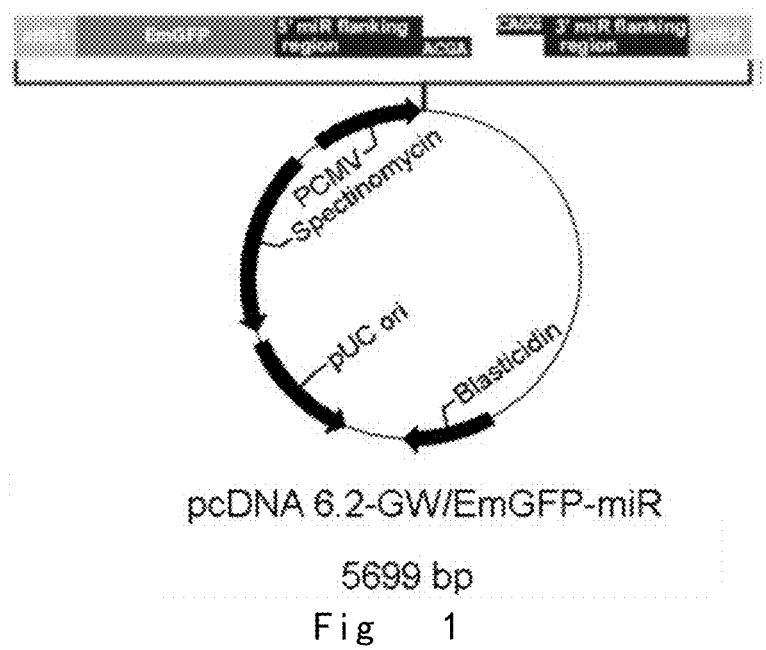
FIG. 1 is a schematic of the plasmid before modification.

The inventor initiates the design and preparation of precursor siRNAs capable of efficiently expressing the K-RAS siRNAs by extensive and deep studies. The precursor siRNAs of the present invention, after having been processed by a host cell, can efficiently express the K-RAS siRNAs, so as to effectively avoid the interference effect of the reverse complementary sequence of a target sequence on the functioning of the target sequence. The experiment demonstrated that the precursor siRNAs of the present invention can efficiently express the K-RAS siRNA sequences, and have a more effective therapeutic effect on various malignant tumours. The present invention is accomplished on this basis.

siRNAs and its Precursors

As used herein, the "siRNAs" refer to a class of RNA molecules, which are obtained by processing transcripts which can form siRNA precursors. The mature siRNAs generally have 18-26 nucleotides (nt) (more specifically, about 19-22 nt), not excluding siRNA molecules having other numbers of nucleotides. siRNAs are usually detectable by northern blotting.

The siRNAs derived from humans can be isolated from human cells. As used herein, "isolated" means that the substance is isolated from its original environment (if it is a natural substance, the original environment is the natural environment). For example, polynucleotides and polypeptides in the natural environment of living cells are not isolated and purified, but when the same polynucleotides or polypeptides are isolated from other substances coexisting in the natural environment, they are isolated and purified.

siRNAs can be obtained by processing the precursor siRNAs, and the said precursor siRNAs can be folded into a stable stem-loop (hairpin) structure having a general length of 50-100 bp. The said precursor siRNAs can be folded into a stable stem-loop structure, and two sides of the stem of the stem-loop structure contain two sequences substantially complementary to each other.

In the present invention, the said precursor siRNAs are artificially synthesised precursor siRNAs, and the said precursor siRNAs have the structure as shown in formula I:

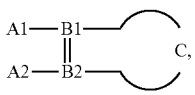

Formula I

As a representative example, B1 is K-RAS siRNA sense strand sequence;

B2 is a sequence with complementarity (including substantial and complete complementarity) to B1;

C is a sequence as shown (GUUUUGGCCA-CUGACUGAC);

A1 and A2 are null or optionally nucleotide sequences consisting of 4-5 bases respectively;

wherein the precursor siRNA as shown can be processed in the host to form the K-RAS siRNA.

In the present invention, the precursor siRNA forming K-RAS siRNA can be spliced to generate an siRNA regulating the K-RAS, i.e. the K-RAS siRNA (for example SEQ ID NO.: 263).

In Formula I, B2 and B1 have substantial complementarity to each other. As used herein, "substantial complementarity" means that the nucleotide sequence is sufficiently complementary and that same can act upon each other in a predictable manner, e.g., forming a secondary structure (such as a stem-loop structure). Generally, at least 70% of nucleotides in two "substantially complementary" nucleotide sequences are complementary; preferably, at least 80% of nucleotides are complementary; and more preferably, at least 90% of nucleotides are complementary. Generally, there are at most 8 non-matched nucleotides, preferably 1, 2, 3, 4 and 5 non-matched nucleotides, between two sufficiently complementary molecules.

As used in the present application, the "stem-loop" structure, also known as the "hairpin" structure, refers to a nucleotide molecule which can form a secondary structure comprising a double-stranded region (stem) formed of two regions (on a same molecule) of this nucleotide molecule, the two regions being at two sides of the double-stranded part; and the structure further comprises at least one "loop" structure, including non-complementary nucleotide molecules, i.e., a single-stranded region. Even if the two regions of the nucleotide molecule are not completely complementary, the double-stranded part of the nucleotide can also maintain the double-stranded form. For example, insertion, deletion, substitution or the like may lead to a non-complementary small region or make the small region itself form a stem-loop structure or another form of secondary structure. However, the two regions can still be substantially complementary to each other and act upon each other in a predictable manner to form a double-stranded region of the stem-loop structure. The stem-loop structure is well known to a person skilled in the art, who can generally determine, when given a nucleic acid having a nucleotide sequence of the primary structure, whether the nucleic acid can form a stem-loop structure.

In the present invention, a "stem-loop structure" can be present at the end of the precursor siRNAs as shown in Formula I, for example, after B1 and B2 form a substantially complementary structure, C will form a stable stem-loop structure at the end thereof; the "stem-loop structure" can also be present in the interior of the precursor siRNAs as shown in Formula I, for example, since B1 and B2 are not completely complementary, the bases in B1 or B2 which do not bind with the others in a complementary manner will form an internal loop.

Highly expressing K-RAS as used herein refers to highly expressing the K-RAS protein, or highly expressing the K-RAS mRNA.

Referring to the siRNA sequences provided in the present invention, polynucleotide constructs, which can, after introduction, be processed into siRNAs capable of affecting the expression of the corresponding mRNAs, can be designed, i.e., the polynucleotide constructs can up-regulate the level of the corresponding K-RAS siRNAs in vivo so as to decrease the expression amount of K-RAS. Therefore, the present invention provides an isolated polynucleotide (construct), and the polynucleotide (construct) can be transcribed by human cells into precursor siRNAs which can be spliced and expressed as the siRNAs in human cells.

Polynucleotide Constructs

As a preferred mode of the present invention, the polynucleotide construct contains a structure from the 5' terminus to the 3' terminus as shown in formula II:

a1-b1-c-b2-a2   Formula II

In Formula II, b1 is a nucleotide sequence which can be expressed as the K-RAS siRNA in a cell, b2 is a nucleotide sequence substantially or completely complementary to b1; c is a spacer sequence between b1 and b2, and the spacer sequence is not complementary to B1 and B2;

a1 and a2 are null or optionally nucleotide sequences consisting of 4-5 bases respectively;

and after being introduced into the cell, the structure as shown in formula II forms a secondary structure as shown in formula I:

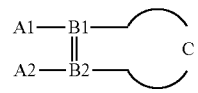

Formula I

Generally, the polynucleotide constructs are located on the expression vector. Therefore, the present invention further includes a vector containing the siRNAs or the polynucleotide constructs. The expression vector typically further contains a promoter, an origin of replication and/or a marker gene, etc. Methods well known to a person skilled in the art can be used to construct the expression vector required by the present invention. These methods include in vitro recombinant DNA technology, DNA synthesis technology, in vivo recombination technology, etc. The expression vector preferably contains one or more selectable marker genes to provide a phenotypic trait for the selection of transformed host cells, such as kanamycin, gentamicin, hygromycin or ampicillin resistance.

In the present invention, there is no special limitation on the said expression vector, including commercially available or conventionally prepared expression vectors. Representative examples include (but are not limited to): pcDNATM6.2-GW/miR, pcDNA3, pMIR-REPORT miRNA, pAdTrack-CMV, pCAMBIA3101+pUC-35S, pCMVp-NEO-BAN, pBI121, pBin438, pCAMBIA1301, pSV2, a CMV4 expression vector, pmiR—RB-Report™, pshOK-basic, mmu-mir 300-399 miRNASelect™, pshRNA-copGFP Lentivector, GV317, GV309, GV253, GV250, GV249, GV234, GV233, GV232, GV201, GV159 or other expression vectors of the GV series.

In another preferred example, in the said expression vector, the promoter operably linked to the polynucleotide expressing the precursor siRNAs includes a constitutive promoter or a tissue-specific promoter, preferably a liver tissue-specific promoter. In other words, these promoters are used to drive the expression of the precursor siRNAs.

Representative promoters includes (but are not limited to): a Pcmv promoter, U6, H1, a CD43 promoter, a CD45 (LCA) promoter, a CD68 promoter, an Endoglin (CD105) promoter, a Fibronectin promoter, an Flt-1 (VEGFR-1) promoter, a GFAP promoter, a GPIIb (Integrin αIIb) promoter, an ICAM-2 (CD102) promoter, an MB (Myoglobin) promoter, an NphsI (Nephrin) promoter, an SPB promoter, an SV40/hAlb promoter, an SYN1 promoter, a WASP promoter or a combination thereof.

Pharmaceutical Composition and Administration Methods

As used herein, the term "effective amount" or "effective dose" refers to the amount which can induce a function or activity in humans and/or animals and can also be acceptable to humans and/or animals.

As used herein, the term "pharmaceutically acceptable" component is applicable to human and/or mammals without excessive adverse side effects (such as toxicity, irritation and allergic responses), i.e., a substance with a reasonable benefit/risk ratio. The term "pharmaceutically acceptable carrier" refers to a carrier for the administration of a therapeutic agent, including various excipients and diluents.

The pharmaceutical composition of the present invention contains a safe and effective amount of the active component of the present invention and a pharmaceutically acceptable carrier. Such carrier includes, but is not limited to, saline, a buffer, glucose, water, glycerol, ethanol, and a combination thereof. Generally, a pharmaceutical preparation shall match the administration mode, and the dosage form of the pharmaceutical composition of the present invention can be an injection, an oral preparation (a tablet, a capsule, or an oral liquid), a transdermal agent, or a slow release agent. For example, preparation thereof is performed by a conventional method using physiological saline or an aqueous solution containing glucose and other adjuvants. The pharmaceutical composition is preferably produced under sterile conditions.

The effective amount of the active component of the present invention may vary depending on the administration mode and the severity of the disease to be treated. A person skilled in the art could determine the selection of the preferred effective amount depending on various factors (e.g., by clinical trials). The factors include, but are not limited to, the pharmacokinetic parameters of said active component, e.g., the bioavailability, metabolism, half-life, etc.; and the severity of the patient's disease to be treated, the patient's weight, the patient's immune state, the administration route, etc. Generally, when the active component of the present invention is administered at a dose of about 0.00001-50 mg/kg body weight (preferably 0.0001-10 mg/kg body weight) per day, satisfactory results can be achieved. For example, due to the urgent requirements of the treatment status, several separate doses can be administered daily, or the dosage can be reduced proportionally.

The pharmaceutically acceptable carrier of the present invention includes (but is not limited to): water, saline, liposomes, lipids, micro particles, micro vesicles, exosomes, shedding vesicles, nanocapsules/nanoparticles, β-cyclodextrin capsule (β-cyclodextriniclusion compound) proteins, protein-antibody conjugates, peptides, cellulose, nanogels, or a combination thereof. The choice of carriers should match the administration mode, which is well known to a person skilled in the art.

In the present invention, the said expression vector can be directly administered to a subject, and the expression vector can also be administered by preparing same into a pharmaceutical composition with a pharmaceutically acceptable carrier. The administration comprises intravenous injection.

Therapeutic Method

The present invention also provides a method for treating diseases associated with the expression amount of the K-RAS siRNA, that is, administering a safe and effective amount of the expression vector or the pharmaceutical composition of the present invention to a subject in need, so as to treat diseases associated with the K-RAS activity. Generally, "a disease associated with the expression amount of the K-RAS siRNA" means that there is a significant difference in the expression amount (or activity) E1 of the K-RAS protein or mRNA, and the K-RAS amount (or activity) E0 in the paracancerous tissue or normal tissue in a patient with the disease, and preferably, the high expression refers to $E1 \geq 1.5\ E0$, and more preferably $E1 \geq 2\ E0$. In tumour tissue, whether K-RAS is highly expressed can be detected by conventional methods. Generally, the malignant tumours highly expressing K-RAS include (but are not limited to) liver cancer, lung cancer, stomach cancer, oesophageal cancer, ovarian cancer, colorectal cancer, cervical cancer, pancreatic cancer, prostatic cancer, leukaemia or breast cancer.

Beneficial Effects of the Present Invention

The precursor siRNAs of the present invention can effectively avoid the over-expression of the reverse complementary sequence of a target sequence along with the over-expression of the target sequence, so as to effectively avoid the interference effect of the reverse complementary sequence of a target sequence on the functioning of the target sequence.

The precursor siRNAs of the present invention can efficiently express K-RAS siRNA sequences, and have an effective therapeutic effect on various malignant tumours, and can thereby be used in the development of novel tumour therapeutic drugs.

The present invention is further illustrated in connection with particular embodiments as follows. It should be understood that these embodiments are merely illustrative of the invention and are not intended to limit the scope of the present invention. In the case of specific conditions for the experimental method being not specified in the following examples, generally conventional conditions are followed, such as the conditions described in Sambrook et al., Molecular Cloning: A Laboratory Manual (New York: Cold Spring Harbour Laboratory Press, 1989), or the conditions recommended by the manufacturer are followed. All percentages and portions are of weight unless otherwise indicated.

Example 1. Construction of the Expression Vector

Figure 2:
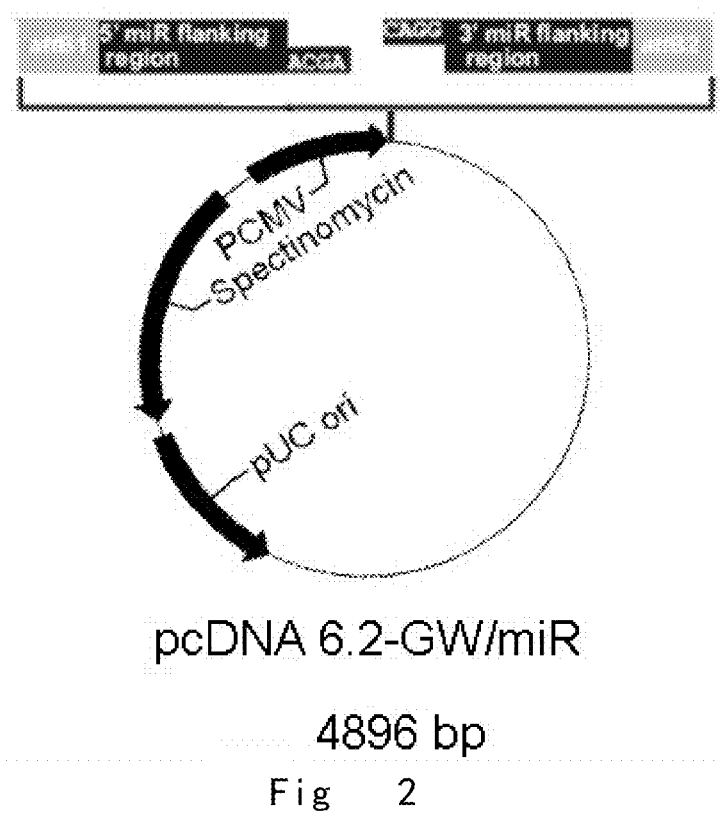
FIG. 2 is the modified plasmid after cutting EmGFP and Blasticidin.

Out of biosafety reasons, the plasmid was first modified. Biologically toxic elements, such as EmGFP and Blasticidin, were cut with DNA restriction endonucleases. FIG. 1 is a schematic of the plasmid before modification. FIG. 2 shows the plasmid after cutting EmGFP and Blasticidin;

pCMV represents a eukaryotic promoter, pUC ori represents the replication origin of the plasmid in prokaryotic cells which does not express an insertion sequence, and Spectinomycin represents the spectinomycin resistance gene for plasmid screening.

After the plasmid modification, a complementary oligo DNA is designed and synthesised according to the K-RAS gene sequence. The K-RAS siRNA sequence was as follows: 5'-GGUGACUUAGGUUCUAGAU-3' (SEQ ID NO: 263). The sequences are as shown in Table 1.

100 µl competent cells were transformed with 10 µl ligated product, followed by spreading on LB plates (containing 50 µg/ml spectinomycin) and incubating at 37° C.

Wherein the strain of competent cells can be *E. coli* DH5α, XL10-GOLD, BB4, DE3, BM25.5, BMH71-

TABLE 1

The oligo DNA sequences and their corresponding precursor siRNA elements

| Oligo name | Oligo DNA sequence 5'-3' |
|---|---|
| | > K-RAS siRNA mature sequence: 5'-GGUGACUUAGGUUCUAGAU-3' |
| 13MR0041-1F | TGCTGAATTC<u>GGTGACTTAGGTTCTAGAT</u>GTTTTGGCCACTGACTGAC<u>ATCTAGAATAAGT CACCA</u><br>\| A1 \| B1 \| C \| B2 \|<br>TGCTGAATTCGGTGACUUAGGUUCUAGAUGTTTTGGCCACTGACTGACATCTAGAATAAG TCACCA) |
| 13MR0041-1R | CCTGACCGGTGGTGACTTATTCTAGATGTCAGTCAGTGGCCAAAACATCTAGAACCTAAG TCACC<br>\| A2 \| B2 \| C \| B1 \|<br>CCTGACCGGTGGTGACTTATTCTAGATGTCAGTCAGTGGCCAAAACATCTAGAACCTAAG TCACC) |
| | Negative control sequence |
| Negative-F | tgctgAAATGTACTGCGCGTGGAGACGTTTTGGCCACTGACTGACGTCTCCACGCAGTACATTT<br>\|A1 \| multiple cloning site \| C \| multiple cloning site \|<br>tgctgAAATGTACTGCGCGTGGAGACGTTTTGGCCACTGACTGACGTCTCCACGCAGTACAT TT) |
| Negative-R | cctgAAATGTACTGCGTGGAGACGTCAGTCAGTGGCCAAAACGTCTCCACGCGCAGTACATTTc<br>\|A2\| multiple cloning site \| C \| multiple cloning site \|<br>cctgAAATGTACTGCGTGGAGACGTCAGTCAGTGGCCAAAACGTCTCCACGCGCAGTACATT Tc) |

Then the synthesised oligo single-stranded DNAs were dissolved in ddH₂O to 100 µM, and 5 µl of each of the complementary single strands were taken and mixed pairwise, and annealed in the system given in Table 2. 2 portions of the oligo mixture were heated at 95° C. for 5 minutes, and then placed at room temperature for 20 minutes to form double-stranded DNAs.

TABLE 2

| Oligo DNA annealing system | |
|---|---|
| 100 µM top strand oligo | 5 µl |
| 100 µM bottom strand oligo | 5 µl |
| 10 × oligo annealing buffer | 2 µl |
| ddH₂O | 8 µl |
| Total volume | 20 µl |

The annealed double-stranded DNAs were then diluted to a concentration of 10 nM, and ligated at room temperature in the system given in Table 3 for 30 minutes.

TABLE 3

| Enzyme ligation system | |
|---|---|
| 5 × ligation buffer | 4 µl |
| pcDNA6.2-GW/EmGFP-miR | 2 µl |
| ds oligo (10 nM) | 4 µl |
| T4 DNA ligase (1 U/µl) | 1 µl |
| ddH₂O | 9 µl |
| Total volume | 20 µl |

18mutS, BW313, C-la, C600, DH1, DH5, DP50supF, ED8654, ED8767, ER1647, HB101, HMS174, JM83, JM101, JM105, JM106, JM107, JM108, JM109, JM110, K802, K803, LE392, MC1061, MV1184, MV1193, NovaBlue, RR1, TAP90, TG1, TG2, XL1-Blue, x1776, Y-1088, Y-1089, Y-1090 and the like.

*E. coli* DH5a or XL10-GOLD can be preferred in the above strains, and *E. coli* DH5α is the most preferable.

3 clones were respectively picked from each transformation plate, followed by shaking same and extracting plasmids therefrom, and sequencing to validate whether the inserted fragment sequence in the recombinant clones was consistent with the designed oligo single-stranded DNA sequence or not.

Example 2. The Therapeutic Effect of K-RAS siRNAs on the Mouse Lewis Lung Cancer LLC (Lewis Lung Cancer) cell line was provided by School of Life Sciences, Nanjing University. DMEM is a product from Hyclone Corporation. Fetal calf serum is a product from Gibco Corporation. In experiments, LLC cell line was cultured in DMEM complete media containing 10% FBS, 100 ug/ml penicillin and 100 ug/ml streptomycin, in an incubator at 37° C. and with 5% $CO_2$.

Experimental animals were 15 6-week-old C57BL/6 mice, half male and half female, provided by the Model Animal Institute, Nanjing University.

LCC cells were first cultured, and the LCC cells grown to the logarithmic phase were digested with pancreatin, followed by centrifuging at 1000 rpm, discarding the supernatant, washing twice with sterile normal saline, suspending the cells in normal saline, trypan blue staining for observing the cell viability, performing the cell counting, and adjusting the cell density to $5\times10^6$ cells/ml. In experiments, healthy C57BL/6 mice were taken and injected at 0.2 ml/mouse through tail-vein slowly, and after the injection was finished, all the modelled mice were divided into:

group 1: mice injected with PBS through the tail-vein slowly (negative control group);

group 2: mice injected with the control plasmid (5 mg/kg) through the tail-vein slowly; and group 3: mice injected with the K-RAS siRNA plasmid (5 mg/kg) through the tail-vein slowly.

In addition, another group of normal mice was taken and used as the normal control. During the model construction, the spirit, dietary statuses, defecation, body weights, activities and other conditions of C57BL/6 mice were observed periodically. Starting from day 14, the mice were administered with 0.1 ml/10 g body weight by intravenous tail injection, and the control group was administered with the corresponding amount of normal saline. During administration, the mice were administered with same once every 3 days, 7 times in total. On day 3 after the last administration, the mice were anaesthetized with diethyl ether, followed by taking the blood, lung and liver. The lung and liver were placed in 10% formalin, pathological sections were made, and the lung cancer model construction situation, and the treatment situation of the K-RAS siRNA plasmid on the lung cancer were observed.

During model construction, the living conditions of all animals were good, and adverse effects such as piloerection, dull-looking, abnormal respiration, slow activity and abnormal stool were not seen.

All the measurement data were expressed as $\bar{\chi}\pm SD$. SPSS 16.0 software package was used for statistical analysis and processing, comparison among multiple groups was performed with variance analysis F test, and comparison among groups was performed with grouping t test, with $P<0.05$ as having statistical significance.

Figure 3:
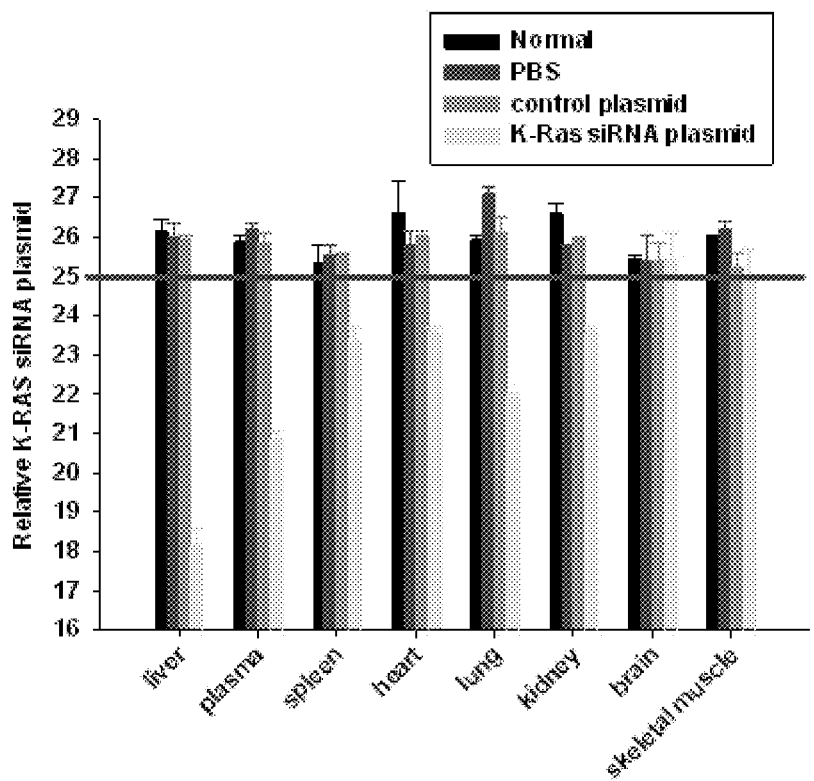
FIG. 3 is a schematic showing the $C_T$ value of the K-RAS siRNA content in various tissues and organs.

Two weeks after the C57BL/6 mice were used for Lewis lung cancer model construction, the K-RAS siRNA plasmid was administered by intravenous injection for treatment; during administration, the mice were administered with same once every 3 days; and the animals were sacrificed on day 3 after the final administration, for taking the blood, lung, liver and various tissues and organs. The K-RAS siRNA content in various tissues and organs was detected by qRT-PCR. FIG. 3 shows the $C_T$ value of the K-RAS siRNA content in various tissues and organs. In FIG. 3, each set of histograms from left to right were Normal, PBS, the control plasmid and the EGFR siRNA plasmid. As can be seen from the detection results, in addition to the brain and skeletal muscle, the K-RAS siRNAs also entered other tissues and organs, such as the liver and lung.

Figure 4:
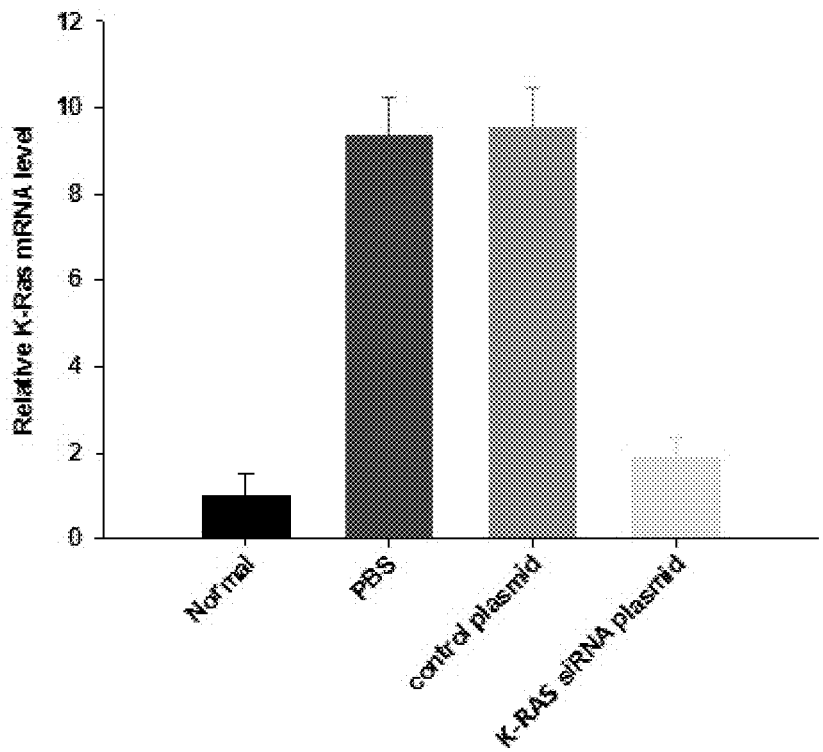
FIG. 4 is a schematic showing the expression level of the K-RAS mRNA in the lung.

FIG. 4 shows the expression level of the K-RAS mRNA in the lung, and the results showed that the K-RAS siRNA significantly reduced the K-RAS mRNA level in the lung tissues and organs.

Figure 5:
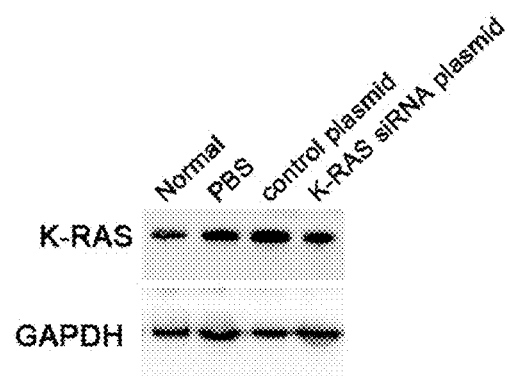
FIG. 5 is an electrophoretogram showing the expression level of the K-RAS protein in the lung.
Figure 6:
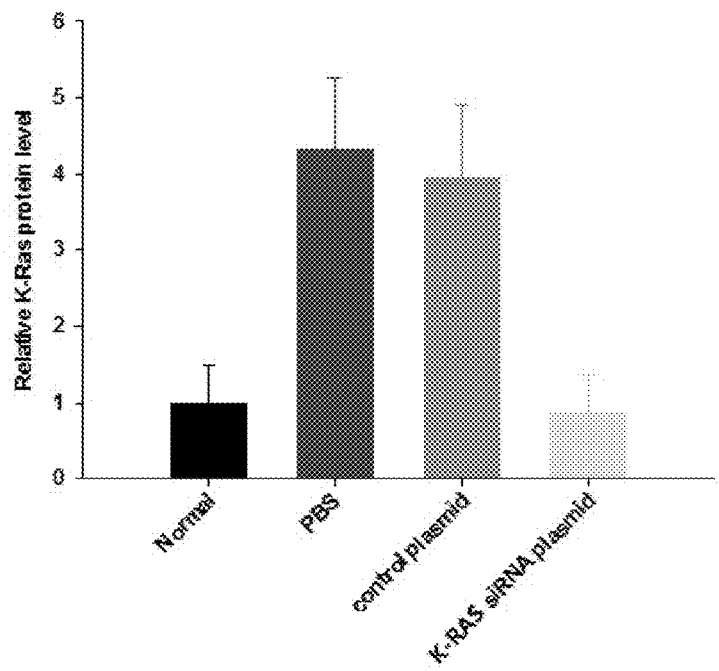
FIG. 6 is a schematic showing the expression level of the K-RAS protein in the lung.

FIG. 5 and FIG. 6 show the expression level of the K-RAS protein in the lung tissues detected using a western blotting experiment after the lung tissue proteins were extracted.

Figure 7:
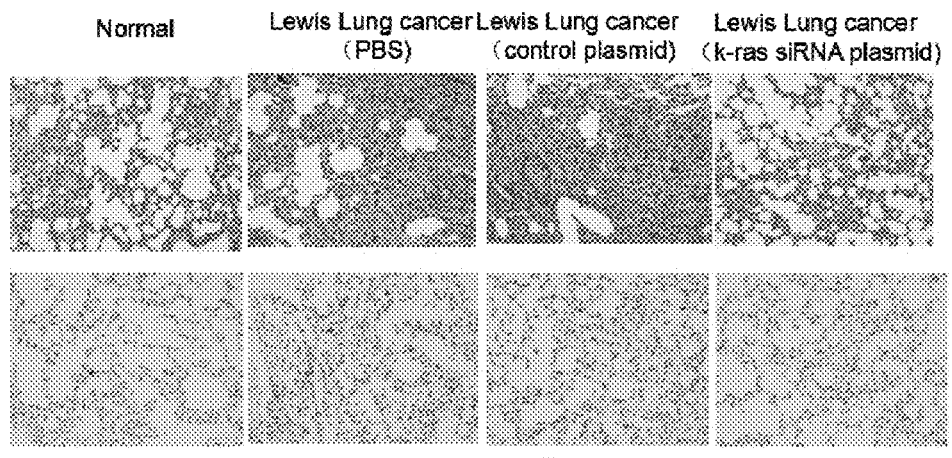
FIG. 7 is a schematic showing the results of pathological sections in the liver and lung of mice.

Besides those for the detection of molecular indicators, the rest of the lung and liver were fixed with formalin, and pathological tissue sections were prepared for examining the tumour situations of the organs. The results of the pathological sections are shown in FIG. 7, wherein tumour lesions were not seen in all the liver sections in each group. In the lung, tumour cell foci with a flake-shaped nucleus being stained largely and deeply to different extents can be seen in each treatment group.

The results above showed that the K-RAS siRNA plasmid can significantly reduce the expression level of the K-RAS protein in the lung tumour tissues.

Figure 8:
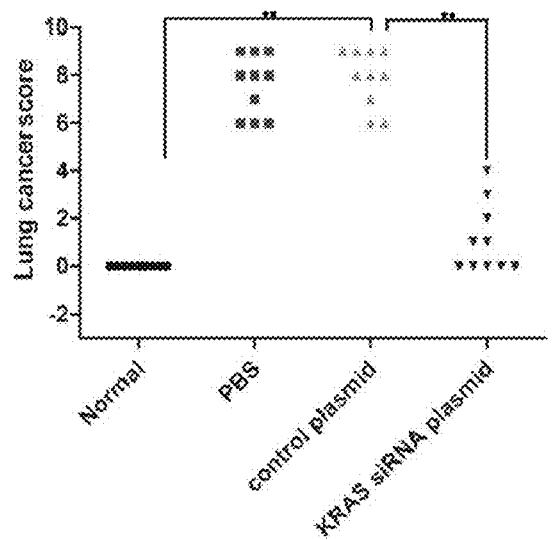
FIG. 8 is a score graph of lung tumour severity.

Example 3. The Study on the Therapeutic Effect of the K-RAS siRNA Plasmid on the Mouse Lewis Lung Cancer Furthermore, we combined the results of all pathological sections to score the severity of lung tumours (results as shown in FIG. 8), showing that the lung tumours in the treatment group were significantly relieved or even cured.

After successful model construction of mouse lung cancer, treatment was performed as the following grouping: control group 1: mice injected with PBS (phosphate buffer) through the tail-vein slowly; control group 2: mice injected with control plasmid (5 mg/kg) (control plasmid not expressing effective K-RAS siRNA precursors) through the tail-vein slowly; experimental group: mice injected with the K-RAS siRNA plasmid (5 mg/kg) through the tail-vein slowly. In addition, another group of normal mice was taken and used as a normal control (Normal).

After treatment, the severity of lung cancer in K-RAS siRNA plasmid mice was significantly lower than that in the two control groups (PBS and control plasmid), and even some mice were completely cured, showing the therapeutic effect of the K-RAS siRNA plasmid on lung tumours.

Figure 9:
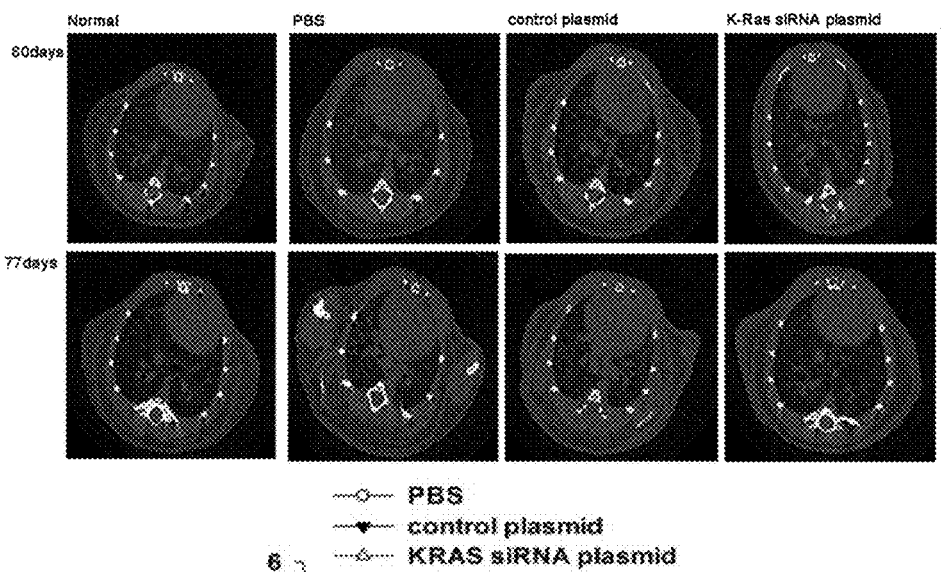
FIG. 9 is a statistical graph showing the diameters of tumours in Example 3.
Figure 9:
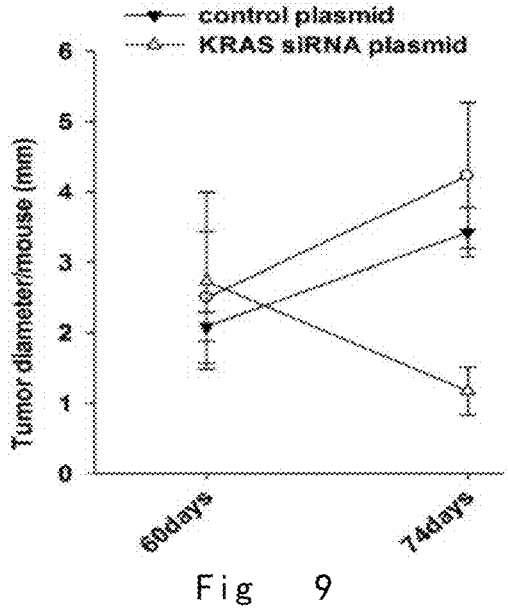

During the treatment, we performed imagological examination on lung tumours in mice utilizing Bruker's Skyscan micro-CT device, and analysed the data using matching statistical software CTAn, to further confirm the therapeutic effect of the KRAS siRNA plasmid on lung tumours. The tumour diameters are as statistically shown in FIG. 9. Compared with the control group, the tumours of KRAS plasmid-treated mice were significantly decreased or even disappeared after treatment, indicating that the KRAS siRNA plasmid has therapeutic effects on lung tumours.

Conclusion

The K-RAS siRNA plasmid had a therapeutic effect on the mouse Lewis lung cancer in vivo, and the abnormal responses related with the medication were not seen during administration.

Example 4. The Therapeutic Effect of the K-RAS siRNA Plasmid on the Mouse Colon Cancer Colon cancer cell line: mouse colon cancer cell line CT-26 (derived from BALB/c, H-2Kd) provided by the College of Life Sciences, Nanjing University.

Experimental animals for model construction: 6-7 week-old female BALB/c mice provided by the Model Animal Institute, Nanjing University.

Animal model construction: BALB/c mice were the same species of animals as the CT-26 tumour cell line. The recovered CT-26 cells were subcultured. When the cells grew to a certain amount, cells in logarithmic growth phase were taken and 0.9% normal saline was added to adjust the cell concentration to $5\times10^6$/ml, the tumour cells were inoculated in the right axilla of the mice subcutaneously at a dose of 0.2 ml/mouse (about $1\times10^6$ cells/mouse), and the mice were fed with a normal diet after inoculation.

1 week later, tumour growth was observed in the axilla of all 15 tumour-bearing BALB/c mice, i.e., the model construction was successful. 15 mice were selected and randomly divided into:

group 1: mice injected with PBS in the left axilla subcutaneously (the negative control group);

group 2: mice injected with control plasmid (5 mg/kg) in the left axilla subcutaneously; and group 3: mice injected with the K-RAS siRNA plasmid (5 mg/kg) in the left axilla subcutaneously.

In addition, another group of normal mice was taken and used as a normal control (Normal).

During model construction, the living status, tumour size and appearance of the BALB/c tumour-bearing mice were observed periodically. Starting from day 8, the mice were administered with 0.1 ml/10 g body weight by intravenous tail injection, and the control group was administered with the same amount of normal saline. During administration, the mice were administered with same once every 3 days, 7 times in total. On day 3 after the final administration, all the mice were sacrificed by spinal dislocation, the skin was incised quickly at the site of tumour growth, and the tumour was completely excised.

The therapeutic effect of the K-RAS siRNA plasmid on the mouse colon cancer was then verified.

1. The effect of the K-RAS siRNA plasmid on the volume of colon cancer subcutaneous transplanted tumours in mice The long diameter (a) and short diameter (b) of tumours were measured with a vernier caliper, and the tumour volume V (mm$^3$) was calculated as $1/6\pi ab^2$. After the measurement, the tumours were fixed in 10% formaldehyde.

The tumour inhibition rate was calculated: tumour inhibition rate (%)=(V in control group−V in experimental group)/V in control group×100%.

Compared with the tumour volume in group 1 and group 2, the volume in group 3 was significantly smaller (P<0.05), as shown in Table 4 below.

TABLE 4

Tumour volumes and tumour inhibition rates in different groups of experimental mice

| Group n | Tumour volume (V/mm$^3$) | average Tumour inhibition rate (%) |
|---|---|---|
| Group 1 | 3768.15 ± 696.13 | 0 |
| Group 2 | 3659.73 ± 951.13 | 0 |
| Group 3 | 2392.75 ± 559.21 | 34.6%*, 36.5%# |

*Relative to group 2,
relative to group 1

The K-RAS siRNA content in the transplanted tumours was detected by qRT-PCR, and the results showed that the K-RAS siRNA entered the transplanted tumours.

Figure 10:
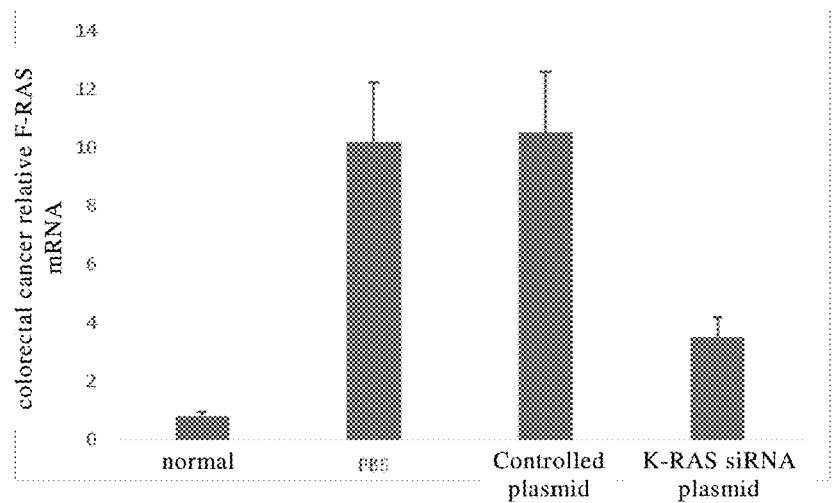
FIG. 10 is a schematic showing the expression level of the K-RAS mRNA in transplanted tumours of colon cancer.

The expression level of the K-RAS mRNA in the transplanted tumours was then detected, and the experimental results (FIG. 10) showed that the K-RAS siRNA plasmid significantly reduced the K-RAS mRNA level in the transplanted tumours.

Figure 11:
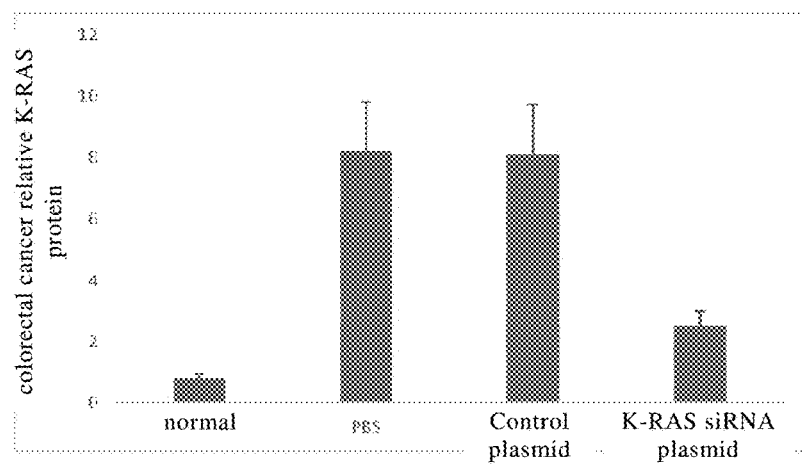
FIG. 11 is a schematic showing the expression level of the K-RAS protein in transplanted tumours the colon cancer.

The tumour tissue proteins were extracted, and the expression level of the K-RAS protein in tumour tissues was detected using a western blotting experiment. It was found from the experimental results (see FIG. 11) that the K-RAS siRNA plasmid had significantly reduced the K-RAS protein in the transplanted tumour tissues.

The K-RAS siRNA plasmid had a therapeutic effect on the colon cancer in vivo, and the abnormal responses related with the medication were not seen during administration.

Example 5. The Therapeutic Effect of the K-RAS siRNA Plasmid on the Mouse Pancreatic Cancer PATU8988, a human pancreatic cancer cell line, was provided by ATCC.

RPMI-1640 complete medium and fetal bovine serum were provided by GIBCO. In the experiment, the human pancreatic cancer cell line was placed in 10% RPMI-1640 complete medium and cultured in an incubator at 37° C., 5% $CO_2$; the medium was changed once every 2 days; and on days 2-3, the cells were digested with 0.25% trypsin and subcultured at a ratio of 1:3.

The experimental animals were 15 half-male and half-female 6-week-old nude BALB/c (nu/nu) mice provided by Beijing Weitong Lihua Laboratory Animal Technology Co., Ltd.

When the human pancreatic cancer cells fully cover the bottom of the bottle, the single cell suspension was collected, and the mice were injected with 0.2 ml at 5×10$^6$ tumour cells/mouse into the pancreas in situ to establish a tumour model.

The pancreatic cancer mice were randomly divided into three groups:

group 1: mice injected with PBS through the tail-vein slowly (negative control group);

group 2: mice injected with the control plasmid (5 mg/kg) through the tail-vein slowly; and group 3: mice injected with the K-RAS siRNA plasmid (5 mg/kg) through the tail-vein slowly.

In addition, another group of normal mice was taken and used as the normal control. During model construction, the spirit, dietary status, defecation, body weight, activity and other conditions of the nude BALB/c (nu/nu) mice were observed periodically. Starting from day 14, the mice were administered with 0.1 ml/10 g body weight by intravenous tail injection, and the control group was administered with the corresponding amount of normal saline. During administration, the mice were administered with same once every 3 days, 7 times in total. On day 3 after the last administration, the mice were anaesthetized with diethyl ether, followed by taking the blood, pancreas and liver. The pancreas and liver were placed in 10% formalin, pathological sections were made, and the pancreatic cancer model construction situation and the treatment effect of the K-RAS siRNA plasmid on the pancreatic cancer were observed.

Two weeks after the BALB/c (nu/nu) mice were used for human pancreatic cancer model construction, the K-RAS siRNA plasmid was administered by intravenous injection for treatment; during administration, the mice were administered with same once every 3 days; and the animals were sacrificed on day 3 after the final administration, for taking the blood, pancreas and liver.

Figure 12:
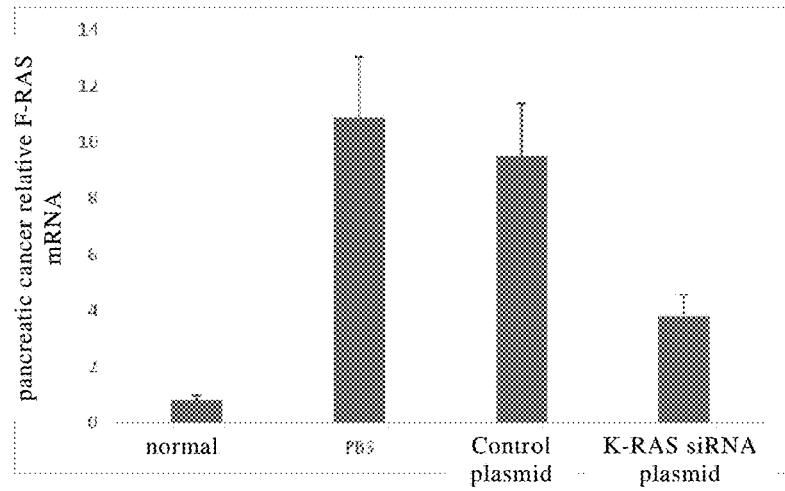
FIG. 12 is a schematic showing the expression level of the K-RAS mRNA in the pancreas.

The expression level of the K-RAS mRNA in the transplanted tumours was then detected, and the experimental results (FIG. 12) showed that the K-RAS siRNA plasmid significantly reduced the K-RAS mRNA level in the transplanted tumours.

Figure 13:
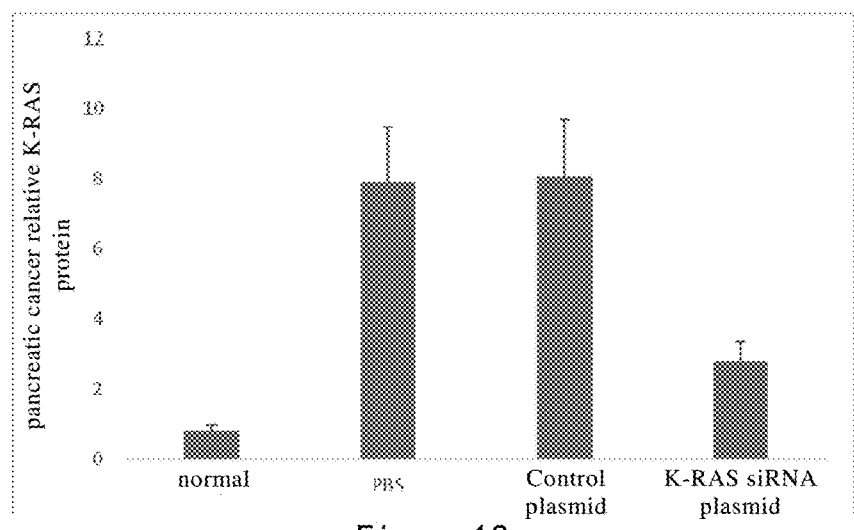
FIG. 13 is a schematic showing the expression level of the K-RAS protein in the pancreas.
Figure 14:
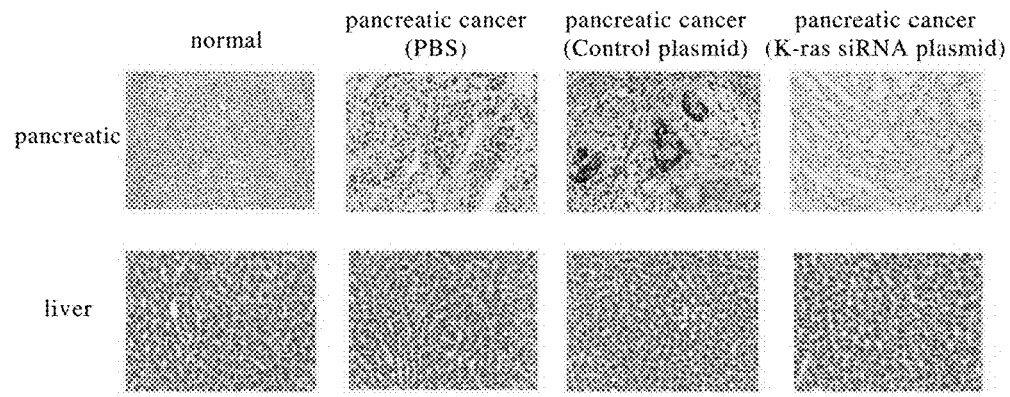
FIG. 14 is a schematic showing the results of pathological sections in the liver and pancreas of mice.

The tumour tissue proteins were extracted, and the expression level of the K-RAS protein in tumour tissues was detected using a western blotting experiment. It was found from the experimental results (see FIG. 13) that the K-RAS siRNA plasmid can significantly reduce the K-RAS protein in the transplanted tumour tissues. The results of the pathological sections are shown in FIG. 14, wherein tumour lesions were not found in all the liver sections in each group. In the pancreas, tumour cell foci with a flake-shaped nucleus being stained largely and deeply to different extents can be seen in each treatment group.

Example 6. Design and Verification of Additional K-RAS siRNA Sequences

Based on the K-RAS siRNA sequence designed in Example 1, up to 260 possible siRNA sequences for multiple sites of the K-RAS gene were further designed in this example, see Table 5 for details. 10 siRNA sequences with excellent stability and evident specific inhibitory effects were further screened from the siRNA sequences above for the expression verification. The sequence numbers of the 10 siRNAs were 3, 26, 41, 47, 52, 73, 88, 98, 101 and 106, respectively.

The expression levels of the K-RAS mRNA and the proteins were verified using the expression vector construction method in Example 1 and the verification method in Example 2, respectively.

Figure 15:
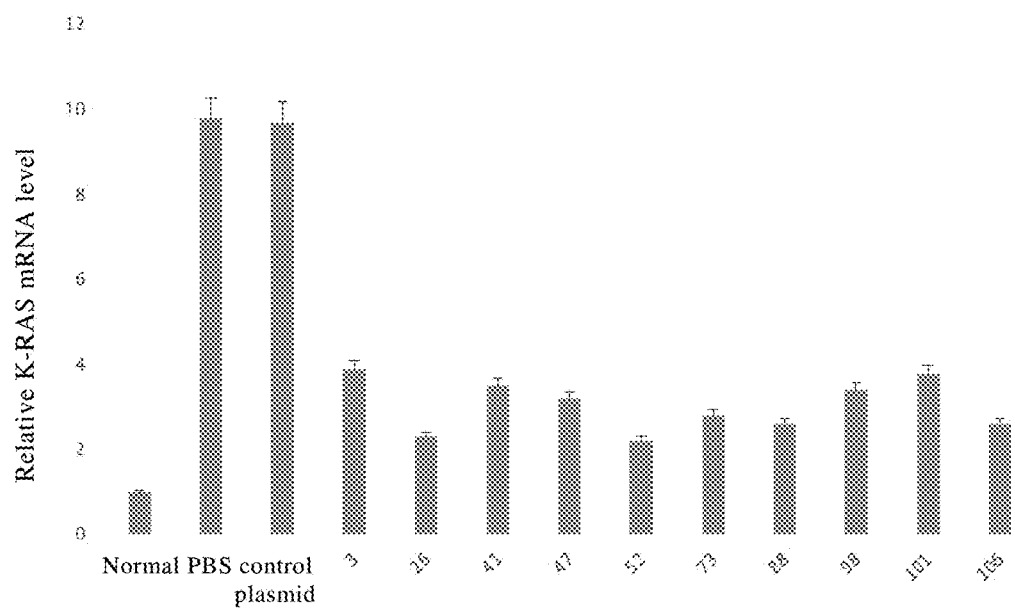
FIG. 15 is a schematic showing the expression level of the K-RAS mRNA in the lung after ten K-RAS siRNAs are introduced.

FIG. 15 shows the expression level of the K-RAS mRNA in the lung, and the results showed that all the plasmids constructed using the screened 10 K-RAS siRNAs reduced the K-RAS mRNA level in the lung tissues and organs.

Figures 16, 17:
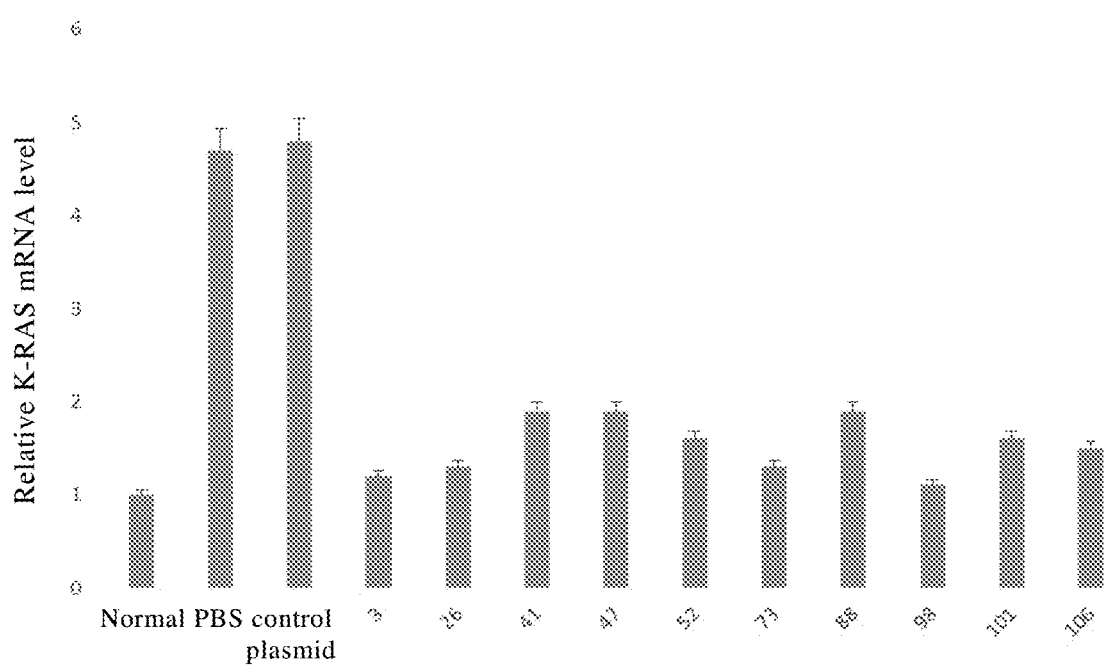
FIG. 16 is a schematic showing the expression level of the K-RAS protein in the lung after ten K-RAS siRNAs are introduced.
FIG. 17 shows the expression level of the K-RAS mRNA in the lung under the action of siRNA I, siRNA II and the siRNA of the present application.

FIG. 16 shows the expression level of the K-RAS protein in the lung tissues detected using a western blotting experiment after the lung tissue proteins were extracted.

The results above showed that the plasmids constructed using the screened 10 K-RAS siRNAs can significantly reduce the expression level of the K-RAS protein in the lung tumour tissues.

TABLE 5

K-RAS siRNA sense strand sequence

| Sequence number | siRNA sense strand |
|---|---|
| 1 | 5' GGCCAGUUAUAGCUUAUUA 3' |
| 2 | 5' GGUCCUAGUAGGAAAUAAA 3' |
| 3 | 5' GCAGCAGCAACAUUAAUAA 3' |
| 4 | 5' GGCAGACCCAGUAUGAAAU 3' |
| 5 | 5' GGUGUGCCAAGACAUUAAU 3' |
| 6 | 5' GGACUCUUCUUCCAUAUUA 3' |
| 7 | 5' GGCAAUGGAAACUAUUAUA 3' |
| 8 | 5' GCAGUUGAUUACUUCUUAU 3' |
| 9 | 5' GGACUUAGCAAGAAGUUAU 3' |
| 10 | 5' GCUCAGCACAAUCUGUAAA 3' |
| 11 | 5' CUCCUUUCCACUGCUAUUA 3' |
| 12 | 5' GCUGUGGAUAUUAUGUAAA 3' |
| 13 | 5' CUCAGCACAAUCUGUAAAU 3' |
| 14 | 5' GUUGGUGUGAAACAAAUUA 3' |
| 15 | 5' GGGCAUGUUAAGUUACAGU 3' |
| 16 | 5' GUGCCAAUUUCUUACUAGU 3' |
| 17 | 5' CACACUGCAUAGGAAUUUA 3' |
| 18 | 5' GCUCUUUCAUAGUAUAACU 3' |
| 19 | 5' CCUGGUAACAGUAAUACAU 3' |
| 20 | 5' GCUCAGGACUUAGCAAGAA 3' |
| 21 | 5' GACUAUGAGUGUGUAUUUA 3' |
| 22 | 5' GCCAUAGACACUAUAGUAU 3' |
| 23 | 5' GGCACUGGGUAUAUGGUAU 3' |
| 24 | 5' GACCCAGAGAUAACACGAU 3' |
| 25 | 5' GAGGAGUACAGUGCAAUGA 3' |
| 26 | 5' GGUAGCAGCAGCAACAUUA 3' |
| 27 | 5' CUCUGUGCCAGCUCUAUAA 3' |
| 28 | 5' GUGCUAGUGUGGUCUGUAA 3' |
| 29 | 5' CUGUACUACUCCUAAUUAU 3' |
| 30 | 5' CUAGUGUGGUCUGUAAUAU 3' |
| 31 | 5' GCAGACGUAUAUUGUAUCA 3' |
| 32 | 5' GGGCUAUAUUUACAUGCUA 3' |
| 33 | 5' GUGCUGUGAAGUGAUCUAA 3' |
| 34 | 5' CCUGUCUCUUGGAUAUUCU 3' |
| 35 | 5' GUGCUGUGGAUAUUAUGUA 3' |
| 36 | 5' GGAGGGCUUUCUUUGUGUA 3' |
| 37 | 5' CUAGGAAUGUUGGUCAUAU 3' |
| 38 | 5' CGUGUUUGCUUAAACUUAA 3' |
| 39 | 5' GCUGAUGCUUUGAACAUCU 3' |
| 40 | 5' GGUCUGUAAUAUCUUACUA 3' |
| 41 | 5' CCUUGACGAUACAGCUAAU 3' |
| 42 | 5' GUGGAUAUCUCCAUGAAGU 3' |
| 43 | 5' CACCAUUAUAGAGAACAAA 3' |
| 44 | 5' GCUUCCUGAUGAUGAUUCU 3' |
| 45 | 5' CAUCCCUGAUGAAUGUAAA 3' |
| 46 | 5' GAAGCAAGUAGUAAUUGAU 3' |
| 47 | 5' GGACGAAUAUGAUCCAACA 3' |
| 48 | 5' GUUCCCAAGUAGGCAUUCU 3' |
| 49 | 5' CCUGACCUCAAGUGAUUCA 3' |
| 50 | 5' GAACUGUACUACUCCUAAU 3' |
| 51 | 5' GUCCUUAGGUAGUGCUAGU 3' |
| 52 | 5' GGCUAUUUCAAGGUCAGAA 3' |
| 53 | 5' CCUGAUGAAUGUAAAGUUA 3' |
| 54 | 5' GUGUCAGACUGCUCUUUCA 3' |
| 55 | 5' CCGAAAUGGAUAUGGAAUA 3' |
| 56 | 5' GACUGCUCUUUCAUAGUAU 3' |
| 57 | 5' CAAGUCUGAUCCAUAUUUA 3' |
| 58 | 5' GAUGAGCAAAGAUGGUAAA 3' |
| 59 | 5' CAAGAGGUGAAGUUUAUAU 3' |
| 60 | 5' GGUAGGGUGUUAAGACUUA 3' |
| 61 | 5' CUAGGCAUCAUGUCCUAUA 3' |

TABLE 5-continued

K-RAS siRNA sense strand sequence

| Sequence number | siRNA sense strand | |  |
|---|---|---|---|
| 62 | 5' | GAGUGAAUGUUCCCAAGUA | 3' |
| 63 | 5' | CCUAGUAGGAAAUAAAUGU | 3' |
| 64 | 5' | GGAAGCAAGUAGUAAUUGA | 3' |
| 65 | 5' | GCUGUGGAUAUCUCCAUGA | 3' |
| 66 | 5' | CCAGAAAUCUUCAUGCAAU | 3' |
| 67 | 5' | GCCUGAACUAGUUCACAGA | 3' |
| 68 | 5' | CAGACGUAUAUUGUAUCAU | 3' |
| 69 | 5' | GUGUAUGUCAGAUAUUCAU | 3' |
| 70 | 5' | GGCUAGUUCUCUUAACACU | 3' |
| 71 | 5' | GAAGGUGACUUAGGUUCUA | 3' |
| 72 | 5' | GAACCUUUGAGCUUUCAUA | 3' |
| 73 | 5' | GCCUUGACGAUACAGCUAA | 3' |
| 74 | 5' | GAGUGCCAAUUUCUUACUA | 3' |
| 75 | 5' | CAGACAAGGAAACUUCUAU | 3' |
| 76 | 5' | CUUCGAUCAAGCUACUUUA | 3' |
| 77 | 5' | GCUACAAAUCAAGAGCAU | 3' |
| 78 | 5' | GUCAUCUCAAACUCUUAGU | 3' |
| 79 | 5' | GUUGUCACCAUUGCACAAU | 3' |
| 80 | 5' | GAUGAUGCCUUCUAUACAU | 3' |
| 81 | 5' | CUGGUAUGAAUAGACAGAA | 3' |
| 82 | 5' | CACUGAGUCACAUCAGAAA | 3' |
| 83 | 5' | GUCAAGCUCAGCACAAUCU | 3' |
| 84 | 5' | GGACUCUGAAGAUGUACCU | 3' |
| 85 | 5' | GGGAUUAUUAUAGCAACCA | 3' |
| 86 | 5' | CUAGGAAGAAGGUGACUUA | 3' |
| 87 | 5' | CUGUGGAUAUCUCCAUGAA | 3' |
| 88 | 5' | GUGGACGAAUAUGAUCCAA | 3' |
| 89 | 5' | CAUGAGUUCUUGAAGAAUA | 3' |
| 90 | 5' | CUGAGUAGCUGGGAUUACA | 3' |
| 91 | 5' | GUGAACCUUUGAGCUUUCA | 3' |
| 92 | 5' | GACAAGGAAACUUCUAUGU | 3' |
| 93 | 5' | CAGUAAUACAUUCCAUUGU | 3' |
| 94 | 5' | CCUGGUAUGAAUAGACAGA | 3' |
| 95 | 5' | GAAUAUAGCAGACGUAUAU | 3' |
| 96 | 5' | CGAUCAAGCUACUUUAUGU | 3' |
| 97 | 5' | GGACAUCACUUACUAUCCA | 3' |
| 98 | 5' | GAAGGUAAUUGAUACACAA | 3' |
| 99 | 5' | CAAGGAAACUUCUAUGUAA | 3' |
| 100 | 5' | GAACCCAGCAGUUACCUUA | 3' |
| 101 | 5' | CAGCAGGCUAUUUCAAGGU | 3' |
| 102 | 5' | CUGAAUACCUAAGAUUUCU | 3' |
| 103 | 5' | GAUCAAGCUACUUUAUGUA | 3' |
| 104 | 5' | GCUCUAUUUAACUGAGUCA | 3' |
| 105 | 5' | CUAGAACAGUAGACACAAA | 3' |
| 106 | 5' | GAUACAGCUAAUUCAGAAU | 3' |
| 107 | 5' | GCAGGCUAUUUCAAGGUCA | 3' |
| 108 | 5' | CCUUAGGUAAUCUAUAACU | 3' |
| 109 | 5' | CCUAACCAUAAGAUUUACU | 3' |
| 110 | 5' | CCUACAGGAAGCAAGUAGU | 3' |
| 111 | 5' | GUGUUGAUGAUGCCUUCUA | 3' |
| 112 | 5' | GCUAUGUGAAACUACAGAU | 3' |
| 113 | 5' | GAAGUAAUGACUCCAUACA | 3' |
| 114 | 5' | CAUCAGAAAUGCCCUACAU | 3' |
| 115 | 5' | CUGCUGUGGAUAUCUCCAU | 3' |
| 116 | 5' | CUCGUUUCUACACAGAGAA | 3' |
| 117 | 5' | CACAUGAGUUCUUGAAGAA | 3' |
| 118 | 5' | GGUUUGGCUAGUUCUCUUA | 3' |
| 119 | 5' | GCUAUAUUUACAUGCUACU | 3' |
| 120 | 5' | CGAAUAUGAUCCAACAAUA | 3' |
| 121 | 5' | CCUCGUUUCUACACAGAGA | 3' |
| 122 | 5' | CCUUUCCACUGCUAUUAGU | 3' |
| 123 | 5' | GACUUAGGCAUUAACAUGU | 3' |
| 124 | 5' | CUCAUUUGUAUUCCAUUGA | 3' |
| 125 | 5' | GAAACUGAAUACCUAAGAU | 3' |
| 126 | 5' | GUGAGGUGAAAGUAUCACU | 3' |
| 127 | 5' | CAAAGACAAAGUGUGUAAU | 3' |
| 128 | 5' | GAGUCACACUGCAUAGGAA | 3' |
| 129 | 5' | GAUGGAGAAACCUGUCUCU | 3' |
| 130 | 5' | GAAAUGCCCUACAUCUUAU | 3' |
| 131 | 5' | GGAUACACUUAUUUGUCAA | 3' |
| 132 | 5' | CAGCAACAUUAAUAAUGGA | 3' |
| 133 | 5' | GAAUGUUGGUGUGAAACAA | 3' |
| 134 | 5' | CUGUUUAGGUAGGGUGUUA | 3' |
| 135 | 5' | GAAUGUUGGUCAUAUCAAA | 3' |
| 136 | 5' | GGAAGAAGGUGACUUAGGU | 3' |
| 137 | 5' | CACAGAGCUAACUGGGUUA | 3' |

TABLE 5-continued

K-RAS siRNA sense strand sequence

| Sequence number | siRNA sense strand | |  |
|---|---|---|---|
| 138 | 5' | GAGAGUUUCACAGCAUGGA | 3' |
| 139 | 5' | GAUAGCUCAACAAGAUACA | 3' |
| 140 | 5' | GCAUAGGAAUUUAGAACCU | 3' |
| 141 | 5' | CACUGAAACUCUUCGAUCA | 3' |
| 142 | 5' | CCAUUUACAUAAGGAUACA | 3' |
| 143 | 5' | CAGUGACUAUGAGUGUGUA | 3' |
| 144 | 5' | GACUAGGGCAGUUUGGAUA | 3' |
| 145 | 5' | CUUUGUGUAUUUGCCAUAA | 3' |
| 146 | 5' | GAGUUAAGGACUCUGAAGA | 3' |
| 147 | 5' | GUCUCUUGGAUAUUCUCGA | 3' |
| 148 | 5' | GGAAGAAUAUAGCAGACGU | 3' |
| 149 | 5' | GACCUAGGAAUGUUGGUCA | 3' |
| 150 | 5' | GACUACUCCUGGUAACAGU | 3' |
| 151 | 5' | GCAGUUACCUUAAAGCUGA | 3' |
| 152 | 5' | GUUCUCUUAACACUGGUUA | 3' |
| 153 | 5' | GUCAAAGACAAAGUGUGUA | 3' |
| 154 | 5' | GCAAGUAGUAAUUGAUGGA | 3' |
| 155 | 5' | CACUGCUAUUAGUCAUGGU | 3' |
| 156 | 5' | CCGAAAGUUUCCAAUUCCA | 3' |
| 157 | 5' | GUGUUGAAGAGACCAAGGU | 3' |
| 158 | 5' | CAUCCAGUGUUGUCAUGCA | 3' |
| 159 | 5' | GACAUCACUUACUAUCCAU | 3' |
| 160 | 5' | GAAGAAUAUAGCAGACGUA | 3' |
| 161 | 5' | CAGUUUGGAUAGCUCAACA | 3' |
| 162 | 5' | GGAUUAUUAUAGCAACCAU | 3' |
| 163 | 5' | CCAAUUUCUUACUAGUACU | 3' |
| 164 | 5' | CCUAAUUAUUACAGCCUUA | 3' |
| 165 | 5' | CUGUACACAUUAAGGUGUA | 3' |
| 166 | 5' | CUGAAACAUUGAGGGAACA | 3' |
| 167 | 5' | CUAGGCUCUAUUUAACUGA | 3' |
| 168 | 5' | CAGUUACCUUAAAGCUGAA | 3' |
| 169 | 5' | CAAUGAGGGACCAGUACAU | 3' |
| 170 | 5' | CUAUAGUAUACCAGUGAAU | 3' |
| 171 | 5' | CCUUCUAGAACAGUAGACA | 3' |
| 172 | 5' | GAAACUGAAUAGCUGUCAU | 3' |
| 173 | 5' | GACUUACACAGUACCUCGU | 3' |
| 174 | 5' | CAGAAGUAAUGACUCCAUA | 3' |
| 175 | 5' | CAACUUGAGUCUUUGAAGA | 3' |
| 176 | 5' | GAAGAGACCAAGGUUGCAA | 3' |
| 177 | 5' | CUUGGAUAUUCUCGACACA | 3' |
| 178 | 5' | GAAAUGGAUAUGGAAUACU | 3' |
| 179 | 5' | GAACUCAUUUAUUCAGCAA | 3' |
| 180 | 5' | CGAUACAGCUAAUUCAGAA | 3' |
| 181 | 5' | GUCAUGCAUUGGUUAGUCA | 3' |
| 182 | 5' | GUCAGAAGUAAUGACUCCA | 3' |
| 183 | 5' | GAUUUCUGAAUUGCUAUGU | 3' |
| 184 | 5' | GAAUCUGACAGAUACCAUA | 3' |
| 185 | 5' | GAGAAUCUGACAGAUACCA | 3' |
| 186 | 5' | GAACUAGCAAUGCCUGUGA | 3' |
| 187 | 5' | GAAAUCUUCAUGCAAUGAA | 3' |
| 188 | 5' | CUUCUAUACAUUAGUUCGA | 3' |
| 189 | 5' | CAUCUCAUUUGUAUUCCAU | 3' |
| 190 | 5' | GAUAGCAUGAAUUCUGCAU | 3' |
| 191 | 5' | GCAUACUAGUACAAGUGGU | 3' |
| 192 | 5' | CUGAAGAUGUACCUAUGGU | 3' |
| 193 | 5' | CAAACCUGGUAUGAAUAGA | 3' |
| 194 | 5' | CAAGAUACAAUCUCACUCU | 3' |
| 195 | 5' | GAAUUGCUAUGUGAAACUA | 3' |
| 196 | 5' | GAUUUGACCUAAUCACUAA | 3' |
| 197 | 5' | CCAAUCCAUUAGCGACAGU | 3' |
| 198 | 5' | CAGAGAAAGAAAUGGCCAU | 3' |
| 199 | 5' | CUUGGCCUCAUAAACCUGU | 3' |
| 200 | 5' | CUAGUUCACAGACAAGGAA | 3' |
| 201 | 5' | CCAUUAGCGACAGUAGGAU | 3' |
| 202 | 5' | CCUACAUCUUAUUUCCUCA | 3' |
| 203 | 5' | CUAUGGUCCUAGUAGGAAA | 3' |
| 204 | 5' | CUGAAAGAAUUCCUUAGGU | 3' |
| 205 | 5' | CUAUGUUACACCAUCUUCA | 3' |
| 206 | 5' | GAAUUCCUUAGGUAAUCUA | 3' |
| 207 | 5' | CACUAUAGUAUACCAGUGA | 3' |
| 208 | 5' | CAUCAGCAAAGACAAGACA | 3' |
| 209 | 5' | CAAGAGGAGUACAGUGCAA | 3' |
| 210 | 5' | GGAAUACUUUAUAAGCCAU | 3' |
| 211 | 5' | CAUGAAUUCUGCAUUGAGA | 3' |
| 212 | 5' | GUUUCCAAUUCCACUGUCU | 3' |
| 213 | 5' | CAUGUCCUAUAGUUUGUCA | 3' |

TABLE 5-continued

K-RAS siRNA sense strand sequence

| Sequence number | | siRNA sense strand | |
|---|---|---|---|
| 214 | 5' | GUGAAAGUAUCACUGGACU | 3' |
| 215 | 5' | GAGUUUCACAGCAUGGACU | 3' |
| 216 | 5' | GUAACAUGUUUACCUGGAA | 3' |
| 217 | 5' | CUGAACUAGUUCACAGACA | 3' |
| 218 | 5' | CUCAAGAGAAUCUGACAGA | 3' |
| 219 | 5' | GUAACAGUAAUACAUUCCA | 3' |
| 220 | 5' | CAAUCCAUUAGCGACAGUA | 3' |
| 221 | 5' | GAAAGAUACUCACAUGAGU | 3' |
| 222 | 5' | CCAAAUGUGUAAUAUUCCA | 3' |
| 223 | 5' | GUUUGGGAUAAUGAUAGGU | 3' |
| 224 | 5' | CAACAAUAGAGGAUUCCUA | 3' |
| 225 | 5' | CAUGAACUGUACUACUCCU | 3' |
| 226 | 5' | GAAACAUUGAGGGAACACA | 3' |
| 227 | 5' | CUCUUGGAUAUUCUCGACA | 3' |
| 228 | 5' | GCAUUAACAUGUUUGUGGA | 3' |
| 229 | 5' | CUGAAUAUAAACUUGUGGU | 3' |
| 230 | 5' | GUAAAGGCGUGUUUGCUUA | 3' |
| 231 | 5' | CUUUGAACAUCUCUUUGCU | 3' |
| 232 | 5' | CCAUACUUCAGGAACUGCA | 3' |
| 233 | 5' | CUAUACAUUAGUUCGAGAA | 3' |
| 234 | 5' | CUUCUAGGCAUCAUGUCCU | 3' |
| 235 | 5' | GAAUACCUAAGAUUUCUGU | 3' |
| 236 | 5' | CAUACUAGUACAAGUGGUA | 3' |
| 237 | 5' | CAUAGGAAUUUAGAACCUA | 3' |
| 238 | 5' | GAAACUAUUAUAAGGCCAU | 3' |
| 239 | 5' | CUUAGCAAGAAGUUAUGGA | 3' |
| 240 | 5' | CUUCUGUGUUAAUACUGGA | 3' |
| 241 | 5' | CUUAAGGCAUACUAGUACA | 3' |
| 242 | 5' | CCUAUAGUUUGUCAUCCCU | 3' |
| 243 | 5' | CUUUGAGCUUUCAUAGAGA | 3' |
| 244 | 5' | CAAGUAGGCAUUCUAGGCU | 3' |
| 245 | 5' | CAAGAGACAUAAUCCCGGU | 3' |
| 246 | 5' | CAAUUCCACUGUCUUGUGU | 3' |
| 247 | 5' | GUUUAUAGCUUAUUAGGUGU | 3' |
| 248 | 5' | GAUAUUCAUAUUGACCCAA | 3' |
| 249 | 5' | CAUAGAGAGUUUCACAGCA | 3' |
| 250 | 5' | GUAAUCUAUAACUAGGACU | 3' |
| 251 | 5' | GAACACAAAUUUAUGGGCU | 3' |
| 252 | 5' | GUUUAUAGGAGUAUGUGCU | 3' |
| 253 | 5' | CAUAAAGGGAUUUGACCUA | 3' |
| 254 | 5' | CAUAAGAUUUACUGCUGCU | 3' |
| 255 | 5' | CUUUGGUAUACGACCCAGA | 3' |
| 256 | 5' | GUAAACUGAAACAUGCACA | 3' |
| 257 | 5' | GGAAACUAUUAUAAGGCCA | 3' |
| 258 | 5' | CAAUUGUGAAUGUUGGUGU | 3' |
| 259 | 5' | CUAAGUGCCAGUAUUCCCA | 3' |
| 260 | 5' | CAUUUGAAGAUAUUCACCA | 3' |
| 261 | 5' | CUUAUUUCCUCAGGGCUCA | 3' |
| 262 | 5' | CAAAUAAACAGGUGCCUGA | 3' |
| 263 | 5' | GGUGACUUAGGUUCUAGAU | 3' |
|  |  |  | 3' |

Comparative Example 1

Two siRNAs (designated siRNA I and siRNA II) that inhibit the K-RAS expression in U.S. Pat. No. 8,008,474 B2 were selected.

siRNA I:
sense strand: 5'-CGAAUAUGAUCCAACAAUA-3';
and antisense strand: 5'-UAUUGUUGGAUCAUAUUCG-3'.

siRNA II:
sense strand: 5'-GAUGAUGCCUUCUAUACAU-3';
and antisense strand: 5'-AUGUAUAGAAGGCAUCAUG-3'.

Plasmid vectors were constructed in the same manner as in Example 1, designated siRNA I plasmid and siRNA II plasmid, respectively. The method in Example 2 was applied to the mouse Lewis lung cancer model, and the expression level of the K-RAS mRNA in each lung was then detected. The experimental results (FIG. 15) showed that, as compared with the siRNA I plasmid and siRNA II plasmid, the K-RAS siRNA plasmid of the present application significantly reduced the K-RAS mRNA level in the lung tissues and organs, indicating that the inhibitory effect thereof was superior to that of the siRNA sequences that inhibit K-RAS in the prior art.

All the documents mentioned in the present invention are incorporatedly referred to, as well as each alone. In addition, it should be understood that after reading the teachings of the present invention described above, a skilled person in the art can make various changes or modifications of the invention, and these equivalent forms shall also fall into the scope of the present application as defined by the appended claims.

The invention claimed is:

1. A precursor sequence having a structure from the 5' terminus to the 3' terminus as shown in formula I:

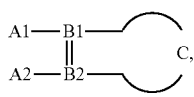

Formula I wherein, B1 is a first ribonucleic acid sequence comprising a K-RAS siRNA sense strand sequence;

B2 is a sequence substantially or completely complementary to B1, and B2 is not complementary to C; wherein substantially complementary means there are 2-8 non-complementary bases between B2 and B1;

C is a stem-loop structure sequence; and

A1 is UGCUG; and/or A2 is CAGG or CAGGA;

wherein the nucleotide sequence of the K-RAS siRNA sense strand is selected from the following sequences as shown in the sequence listing: SEQ ID NO: 263; and the precursor sequence can be processed in a host to form the K-RAS siRNA.

2. The precursor sequence of claim 1, wherein substantially complementary means that there are 3-5 non-complementary bases between B2 and B1.

3. The precursor sequence of claim 2, wherein A1 is UGCUG.

4. A polynucleotide, which can be transcribed by a host to form the precursor sequence of claim 1.

5. An expression vector, comprising the precursor sequence of claim 1 or a polynucleotide that can be transcribed by a host to form said precursor sequence.

6. A pharmaceutical composition, comprising
(a) an expression vector for expression of an siRNA that inhibits K-RAS gene expression; and
(b) a pharmaceutically acceptable carrier;
wherein the expression vector expresses the precursor sequence of claim 1.

7. A method for administering a pharmaceutical composition, comprising
administering the pharmaceutical composition of claim 6 at a first site of a mammal, so that the expression vector is processed to form a microvesicle in the mammal which is transported to a second site on the mammal where the siRNA is expressed.

8. A pharmaceutical composition, comprising
the precursor sequence of claim 1 or
an expression vector, which comprises said precursor sequence or a polynucleotide that can be transcribed by a host to form said precursor sequence, and
a pharmaceutically acceptable carrier.

9. The pharmaceutical composition of claim 8, comprising said expression vector; and/or
the dosage form of the pharmaceutical composition comprises a tablet, a capsule, a powder, a pill, a granule, a syrup, a solution, a suspension liquid, an emulsion, a suspension, an injection solution, or an injectable powder.

10. The pharmaceutical composition of claim 8, wherein the administration mode of the pharmaceutical composition comprises oral, respiratory tract, injection, transdermal, mucosal, or cavity administration.

11. An siRNA for inhibiting expression of a K-RAS gene, wherein the nucleotide sequence of the sense strand of the siRNA is SEQ ID NO: 263, and to which directly or indirectly a sequence A1 and/or A2 is attached, wherein A1 is UGCUG and A2 is CAGG or CAGGA.

12. A method for inhibiting K-RAS or for treating a malignant tumour highly expressing K-RAS;
wherein the malignant tumour is selected from the group consisting of kidney cancer, oral epithelial cancer, head and neck cancer, bladder cancer, brain tumour, glioblastoma, liver cancer, lung cancer, stomach cancer, oesophageal cancer, ovarian cancer, colorectal cancer, cervical cancer, pancreatic cancer, prostatic cancer, leukaemia and breast cancer,
comprising administering to a subject in need thereof an effective amount of the precursor sequence of claim 1, or
an expression vector, comprising said precursor sequence or a polynucleotide that can be transcribed by a host to form said precursor sequence, or
an siRNA capable of inhibiting expression of a K-RAS gene, wherein the nucleotide sequence of the sense strand of the siRNA is SEQ ID NO: 263, and to which directly or indirectly a sequence A1 and/or A2 is attached, wherein A1 is UGCUG and A2 is CAGG or CAGGA.

13. The pharmaceutical composition of claim 9, comprising a plasmid containing the precursor sequence of claim 1.

14. The pharmaceutical composition of claim 9, wherein the dosage form is an injection.

15. The pharmaceutical composition of claim 14, wherein the dosage form is an intravenous injection.

16. The pharmaceutical composition of claim 14, wherein the dosage form is an intraperitoneal injection.

17. The pharmaceutical composition of claim 8, wherein the administration mode of the pharmaceutical composition comprises direct injection of a plasmid.

18. The method according to claim 12, which is for treating kidney cancer, oral epithelial cancer, head and neck cancer, bladder cancer, brain tumour, glioblastoma, liver cancer, lung cancer, stomach cancer, oesophageal cancer, ovarian cancer, colorectal cancer, cervical cancer, pancreatic cancer, prostatic cancer, leukaemia or breast cancer.

19. The precursor sequence of claim 2, wherein substantially complementary means that there are 1-2 bases deleted in B2 compared to B1.

20. The precursor sequence of claim 2, wherein A2 is CAGG or CAGGA.

* * * * *

SEQUENCE LISTING

<160> NUMBER OF SEQ ID NOS: 268

<210> SEQ ID NO 1
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 1
ggccaguuau agcuuauua                                                    19

<210> SEQ ID NO 2
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 2
gguccuagua ggaaauaaa                                                    19

<210> SEQ ID NO 3
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 3
gcagcagcaa cauuaauaa                                                    19

<210> SEQ ID NO 4
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 4
ggcagaccca guaugaaau                                                    19

<210> SEQ ID NO 5
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 5
ggugugccaa gacauuaau                                                    19

<210> SEQ ID NO 6
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 6
ggacucuucu uccauauua                                                    19

<210> SEQ ID NO 7
<211> LENGTH: 19
<212> TYPE: RNA
<213> ORGANISM: Artificial Sequence

```
<220> FEATURE:
<223> OTHER INFORMATION: synthesized nucleotide

<400> SEQUENCE: 7
ggcaauggaa acuauuaua                                              19

<210> SEQ ID NO 8
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 8
gcaguugauu acuucuuau                                              19

<210> SEQ ID NO 9
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 9
ggacuuagca agaaguuau                                              19

<210> SEQ ID NO 10
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 10
gcucagcaca aucuguaaa                                              19

<210> SEQ ID NO 11
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 11
cuccuuucca cugcuauua                                              19

<210> SEQ ID NO 12
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 12
gcuguggaua uuauguaaa                                              19

<210> SEQ ID NO 13
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 13
cucagcacaa ucuguaaau                                              19
```

```
<210> SEQ ID NO 14
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 14
guugguguga aacaaauua                                                19

<210> SEQ ID NO 15
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 15
gggcauguua aguuacagu                                                19

<210> SEQ ID NO 16
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 16
gugccaauuu cuuacuagu                                                19

<210> SEQ ID NO 17
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 17
cacacugcau aggaauuua                                                19

<210> SEQ ID NO 18
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 18
gcucuuucau aguauaacu                                                19

<210> SEQ ID NO 19
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 19
ccugguaaca guaauacau                                                19

<210> SEQ ID NO 20
<211> LENGTH: 19
<212> TYPE: RNA
<213> ORGANISM: Artificial Sequence
<220> FEATURE:
<223> OTHER INFORMATION: synthesized nucleotide
```

```
<400> SEQUENCE: 20
gcucaggacu uagcaagaa                                                  19

<210> SEQ ID NO 21
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 21
gacuaugagu guguauuua                                                  19

<210> SEQ ID NO 22
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 22
gccauagaca cuauaguau                                                  19

<210> SEQ ID NO 23
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 23
ggcacugggu auauggauu                                                  19

<210> SEQ ID NO 24
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 24
gacccagaga uaacacgau                                                  19

<210> SEQ ID NO 25
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 25
gaggaguaca gugcaauga                                                  19

<210> SEQ ID NO 26
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 26
gguagcagca gcaacauua                                                  19

<210> SEQ ID NO 27
```

<211> LENGTH: 19
<212> TYPE: RNA
<213> ORGANISM: Artificial Sequence
<220> FEATURE:
<223> OTHER INFORMATION: synthesized nucleotide

<400> SEQUENCE: 27
cucugugcca gcucuauaa                                                        19

<210> SEQ ID NO 28
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 28
gugcuagugu ggucuguaa                                                        19

<210> SEQ ID NO 29
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 29
cuguacuacu ccuaauuau                                                        19

<210> SEQ ID NO 30
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 30
cuaguguggu cuguaauau                                                        19

<210> SEQ ID NO 31
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 31
gcagacguau auuguauca                                                        19

<210> SEQ ID NO 32
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 32
gggcuauauu uacaugcua                                                        19

<210> SEQ ID NO 33
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 33

```
gugcugugaa gugaucuaa                                                19

<210> SEQ ID NO 34
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 34
ccugucucuu ggauauucu                                                19

<210> SEQ ID NO 35
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 35
gugcugugga uauuaugua                                                19

<210> SEQ ID NO 36
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 36
ggagggcuuu cuuugugua                                                19

<210> SEQ ID NO 37
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 37
cuaggaaugu uggucauau                                                19

<210> SEQ ID NO 38
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 38
cguguuugcu uaaacuuaa                                                19

<210> SEQ ID NO 39
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 39
gcugaugcuu ugaacaucu                                                19

<210> SEQ ID NO 40
<211> LENGTH: 19
<212> TYPE: RNA
```

<213> ORGANISM: Artificial Sequence
<220> FEATURE:
<223> OTHER INFORMATION: synthesized nucleotide

<400> SEQUENCE: 40
ggucuguaau aucuuacua        19

<210> SEQ ID NO 41
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 41
ccuugacgau acagcuaau        19

<210> SEQ ID NO 42
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 42
guggauaucu ccaugaagu        19

<210> SEQ ID NO 43
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 43
caccauuaua gagaacaaa        19

<210> SEQ ID NO 44
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 44
gcuuccugau gaugauucu        19

<210> SEQ ID NO 45
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 45
caucccugau gaauguaaa        19

<210> SEQ ID NO 46
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 46
gaagcaagua guaauugau        19

<210> SEQ ID NO 47
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 47
ggacgaauau gauccaaca                                           19

<210> SEQ ID NO 48
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 48
guucccaagu aggcauucu                                           19

<210> SEQ ID NO 49
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 49
ccugaccuca agugauuca                                           19

<210> SEQ ID NO 50
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 50
gaacuguacu acuccuaau                                           19

<210> SEQ ID NO 51
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 51
guccuuaggu agugcuagu                                           19

<210> SEQ ID NO 52
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 52
ggcuauuuca aggucagaa                                           19

<210> SEQ ID NO 53
<211> LENGTH: 19
<212> TYPE: RNA
<213> ORGANISM: Artificial Sequence
<220> FEATURE:

<223> OTHER INFORMATION: synthesized nucleotide

<400> SEQUENCE: 53
ccugaugaau guaaaguua                                                    19

<210> SEQ ID NO 54
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 54
gugucagacu gcucuuuca                                                    19

<210> SEQ ID NO 55
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 55
ccgaaaugga uauggaaua                                                    19

<210> SEQ ID NO 56
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 56
gacugcucuu ucauaguau                                                    19

<210> SEQ ID NO 57
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 57
caagucugau ccauauuua                                                    19

<210> SEQ ID NO 58
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 58
gaugagcaaa gaugguaaa                                                    19

<210> SEQ ID NO 59
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 59
caagagguga aguuuauau                                                    19

```
<210> SEQ ID NO 60
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 60
gguagggugu uaagacuua                                                    19

<210> SEQ ID NO 61
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 61
cuaggcauca uguccuaua                                                    19

<210> SEQ ID NO 62
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 62
gagugaaugu ucccaagua                                                    19

<210> SEQ ID NO 63
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 63
ccuaguagga aauaaaugu                                                    19

<210> SEQ ID NO 64
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 64
ggaagcaagu aguaauuga                                                    19

<210> SEQ ID NO 65
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 65
gcuguggaua ucuccauga                                                    19

<210> SEQ ID NO 66
<211> LENGTH: 19
<212> TYPE: RNA
<213> ORGANISM: Artificial Sequence
<220> FEATURE:
<223> OTHER INFORMATION: synthesized nucleotide
```

```
<400> SEQUENCE: 66
ccagaaaucu ucaugcaau                                        19

<210> SEQ ID NO 67
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 67
gccugaacua guucacaga                                        19

<210> SEQ ID NO 68
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 68
cagacguaua uuguaucau                                        19

<210> SEQ ID NO 69
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 69
guguauguca gauauucau                                        19

<210> SEQ ID NO 70
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 70
ggcuaguucu cuuaacacu                                        19

<210> SEQ ID NO 71
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 71
gaaggugacu uagguucua                                        19

<210> SEQ ID NO 72
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 72
gaaccuuuga gcuuucaua                                        19

<210> SEQ ID NO 73
<211> LENGTH: 19
```

```
<212> TYPE: RNA
<213> ORGANISM: Artificial Sequence
<220> FEATURE:
<223> OTHER INFORMATION: synthesized nucleotide

<400> SEQUENCE: 73
gccuugacga uacagcuaa                                                        19

<210> SEQ ID NO 74
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 74
gagugccaau uucuuacua                                                        19

<210> SEQ ID NO 75
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 75
cagacaagga aacuucuau                                                        19

<210> SEQ ID NO 76
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 76
cuucgaucaa gcuacuuua                                                        19

<210> SEQ ID NO 77
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 77
gcugacaaau caagagcau                                                        19

<210> SEQ ID NO 78
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 78
gucaucucaa acucuuagu                                                        19

<210> SEQ ID NO 79
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 79
```

| | |
|---|---|
| guugucacca uugcacaau | 19 |

<210> SEQ ID NO 80
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 80

| | |
|---|---|
| gaugaugccu ucuauacau | 19 |

<210> SEQ ID NO 81
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 81

| | |
|---|---|
| cugguaugaa uagacagaa | 19 |

<210> SEQ ID NO 82
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 82

| | |
|---|---|
| cacugaguca caucagaaa | 19 |

<210> SEQ ID NO 83
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 83

| | |
|---|---|
| gucaagcuca gcacaaucu | 19 |

<210> SEQ ID NO 84
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 84

| | |
|---|---|
| ggacucugaa gauguaccu | 19 |

<210> SEQ ID NO 85
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 85

| | |
|---|---|
| gggauuauua uagcaacca | 19 |

<210> SEQ ID NO 86
<211> LENGTH: 19
<212> TYPE: RNA
<213> ORGANISM: Artificial Sequence

```
<220> FEATURE:
<223> OTHER INFORMATION: synthesized nucleotide

<400> SEQUENCE: 86
cuaggaagaa ggugacuua                                                    19

<210> SEQ ID NO 87
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 87
cuguggauau cuccaugaa                                                    19

<210> SEQ ID NO 88
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 88
guggacgaau augauccaa                                                    19

<210> SEQ ID NO 89
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 89
caugaguucu ugaagaaua                                                    19

<210> SEQ ID NO 90
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 90
cugaguagcu gggauuaca                                                    19

<210> SEQ ID NO 91
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 91
gugaaccuuu gagcuuuca                                                    19

<210> SEQ ID NO 92
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 92
gacaaggaaa cuucuaugu                                                    19
```

```
<210> SEQ ID NO 93
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 93
caguaauaca uuccauugu                                                    19

<210> SEQ ID NO 94
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 94
ccugguauga auagacaga                                                    19

<210> SEQ ID NO 95
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 95
gaauauagca gacguauau                                                    19

<210> SEQ ID NO 96
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 96
cgaucaagcu acuuuaugu                                                    19

<210> SEQ ID NO 97
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 97
ggacaucacu uacuaucca                                                    19

<210> SEQ ID NO 98
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 98
gaagguaauu gauacacaa                                                    19

<210> SEQ ID NO 99
<211> LENGTH: 19
<212> TYPE: RNA
<213> ORGANISM: Artificial Sequence
<220> FEATURE:
<223> OTHER INFORMATION: synthesized nucleotide
```

<400> SEQUENCE: 99
caaggaaacu ucuauguaa                                                    19

<210> SEQ ID NO 100
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 100
gaacccagca guuaccuua                                                    19

<210> SEQ ID NO 101
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 101
cagcaggcua uuucaaggu                                                    19

<210> SEQ ID NO 102
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 102
cugaauaccu aagauuucu                                                    19

<210> SEQ ID NO 103
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 103
gaucaagcua cuuuaugua                                                    19

<210> SEQ ID NO 104
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 104
gcucuauuua acugaguca                                                    19

<210> SEQ ID NO 105
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 105
cuagaacagu agacacaaa                                                    19

<210> SEQ ID NO 106

```
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 106
gauacagcua auucagaau                                              19

<210> SEQ ID NO 107
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 107
gcaggcuauu ucagguca                                               19

<210> SEQ ID NO 108
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 108
ccuuagguaa ucuauaacu                                              19

<210> SEQ ID NO 109
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 109
ccuaaccaua agauuuacu                                              19

<210> SEQ ID NO 110
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 110
ccuacaggaa gcaaguagu                                              19

<210> SEQ ID NO 111
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 111
guguugauga ugccuucua                                              19

<210> SEQ ID NO 112
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 112
```
gcuaugugaa acuacagau                                            19

<210> SEQ ID NO 113
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 113
gaaguaauga cuccauaca                                            19

<210> SEQ ID NO 114
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 114
caucagaaau gcccuacau                                            19

<210> SEQ ID NO 115
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 115
cugcugugga uaucuccau                                            19

<210> SEQ ID NO 116
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 116
cucguuucua cacagagaa                                            19

<210> SEQ ID NO 117
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 117
cacaugaguu cuugaagaa                                            19

<210> SEQ ID NO 118
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 118
gguuuggcua guucucuua                                            19

<210> SEQ ID NO 119
<211> LENGTH: 19
<212> TYPE: RNA

<213> ORGANISM: Artificial Sequence
<220> FEATURE:
<223> OTHER INFORMATION: synthesized nucleotide

<400> SEQUENCE: 119
gcuauauuua caugcuacu                19

<210> SEQ ID NO 120
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 120
cgaauaugau ccaacaaua                19

<210> SEQ ID NO 121
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 121
ccucguuucu acacagaga                19

<210> SEQ ID NO 122
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 122 ccuuccacu gcuauuagu                 19

<210> SEQ ID NO 123
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 123
gacuuaggca uuaacaugu                19

<210> SEQ ID NO 124
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 124
cucauuugua uuccauuga                19

<210> SEQ ID NO 125
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 125
gaaacugaau accuaagau                19

<210> SEQ ID NO 126
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 126
gugaggugaa aguaucacu                                              19

<210> SEQ ID NO 127
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 127
caaagacaaa guguguaau                                              19

<210> SEQ ID NO 128
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 128
gagucacacu gcauaggaa                                              19

<210> SEQ ID NO 129
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 129
gauggagaaa ccugucucu                                              19

<210> SEQ ID NO 130
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 130
gaaaugcccu acaucuuau                                              19

<210> SEQ ID NO 131
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 131
ggauacacuu auuugucaa                                              19

<210> SEQ ID NO 132
<211> LENGTH: 19
<212> TYPE: RNA
<213> ORGANISM: Artificial Sequence
<220> FEATURE:

<223> OTHER INFORMATION: synthesized nucleotide

<400> SEQUENCE: 132
cagcaacauu aauaaugga                                                        19

<210> SEQ ID NO 133
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 133
gaauguuggu gugaaacaa                                                        19

<210> SEQ ID NO 134
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 134
cuguuuaggu aggguguua                                                        19

<210> SEQ ID NO 135
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 135
gaauguuggu cauaucaaa                                                        19

<210> SEQ ID NO 136
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 136
ggaagaaggu gacuuaggu                                                        19

<210> SEQ ID NO 137
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 137
cacagagcua acuggguua                                                        19

<210> SEQ ID NO 138
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 138
gagaguuuca cagcaugga                                                        19

```
<210> SEQ ID NO 139
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 139
gauagcucaa caagauaca                                                  19

<210> SEQ ID NO 140
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 140
gcauaggaau uuagaaccu                                                  19

<210> SEQ ID NO 141
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 141
cacugaaacu cuucgauca                                                  19

<210> SEQ ID NO 142
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 142
ccauuuacau aaggauaca                                                  19

<210> SEQ ID NO 143
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 143
cagugacuau gagugugua                                                  19

<210> SEQ ID NO 144
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 144
gacuagggca guuuggaua                                                  19

<210> SEQ ID NO 145
<211> LENGTH: 19
<212> TYPE: RNA
<213> ORGANISM: Artificial Sequence
<220> FEATURE:
<223> OTHER INFORMATION: synthesized nucleotide
```

<400> SEQUENCE: 145
cuuuguguau uugccauaa								19

<210> SEQ ID NO 146
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 146
gaguuaagga cucugaaga								19

<210> SEQ ID NO 147
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 147
gucucuugga uauucucga								19

<210> SEQ ID NO 148
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 148
ggaagaauau agcagacgu								19

<210> SEQ ID NO 149
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 149
gaccuaggaa uguugguca								19

<210> SEQ ID NO 150
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 150
gacuacuccu gguaacagu								19

<210> SEQ ID NO 151
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 151
gcaguuaccu uaaagcuga								19

<210> SEQ ID NO 152
<211> LENGTH: 19

```
<212> TYPE: RNA
<213> ORGANISM: Artificial Sequence
<220> FEATURE:
<223> OTHER INFORMATION: synthesized nucleotide

<400> SEQUENCE: 152
guucucuuaa cacugguua                                              19

<210> SEQ ID NO 153
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 153
gucaaagaca aagugugua                                              19

<210> SEQ ID NO 154
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 154
gcaaguagua auugaugga                                              19

<210> SEQ ID NO 155
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 155
cacugcuauu agucauggu                                              19

<210> SEQ ID NO 156
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 156
ccgaaaguuu ccaauucca                                              19

<210> SEQ ID NO 157
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 157
guguugaaga gaccaaggu                                              19

<210> SEQ ID NO 158
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 158
```
cauccagugu ugucaugca                                              19

<210> SEQ ID NO 159
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 159
gacaucacuu acuauccau                                              19

<210> SEQ ID NO 160
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 160
gaagaauaua gcagacgua                                              19

<210> SEQ ID NO 161
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 161
caguuuggau agcucaaca                                              19

<210> SEQ ID NO 162
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 162
ggauuauuau agcaaccau                                              19

<210> SEQ ID NO 163
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 163
ccaauuucuu acuaguacu                                              19

<210> SEQ ID NO 164
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 164
ccuaauuauu acagccuua                                              19

<210> SEQ ID NO 165
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 165
cuguacacau uaaggugua                                                19

<210> SEQ ID NO 166
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 166
cugaaacauu gagggaaca                                                19

<210> SEQ ID NO 167
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 167
cuaggcucua uuuaacuga                                                19

<210> SEQ ID NO 168
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 168
caguuaccuu aaagcugaa                                                19

<210> SEQ ID NO 169
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 169
caaugaggga ccaguacau                                                19

<210> SEQ ID NO 170
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 170
cuauaguaua ccagugaau                                                19

<210> SEQ ID NO 171
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 171
ccuucuagaa caguagaca                                                19

```
<210> SEQ ID NO 172
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 172
gaaacugaau agcugucau                                              19

<210> SEQ ID NO 173
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 173
gacuuacaca guaccucgu                                              19

<210> SEQ ID NO 174
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 174
cagaaguaau gacuccaua                                              19

<210> SEQ ID NO 175
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 175
caacuugagu cuuugaaga                                              19

<210> SEQ ID NO 176
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 176
gaagagacca agguugcaa                                              19

<210> SEQ ID NO 177
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 177
cuuggauauu cucgacaca                                              19

<210> SEQ ID NO 178
<211> LENGTH: 19
<212> TYPE: RNA
<213> ORGANISM: Artificial Sequence
<220> FEATURE:
<223> OTHER INFORMATION: synthesized nucleotide
```

<400> SEQUENCE: 178
gaaauggaua uggaauacu                                            19

<210> SEQ ID NO 179
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 179
gaacucauuu auucagcaa                                            19

<210> SEQ ID NO 180
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 180
cgauacagcu aauucagaa                                            19

<210> SEQ ID NO 181
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 181
gucaugcauu gguuaguca                                            19

<210> SEQ ID NO 182
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 182
gucagaagua augacucca                                            19

<210> SEQ ID NO 183
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 183
gauuucugaa uugcuaugu                                            19

<210> SEQ ID NO 184
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 184
gaaucugaca gauaccaua                                            19

<210> SEQ ID NO 185

```
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 185
gagaaucuga cagauacca                                                  19

<210> SEQ ID NO 186
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 186
gaacuagcaa ugccuguga                                                  19

<210> SEQ ID NO 187
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 187
gaaaucuuca ugcaaugaa                                                  19

<210> SEQ ID NO 188
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 188
cuucuauaca uuaguucga                                                  19

<210> SEQ ID NO 189
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 189
caucucauuu guauuccau                                                  19

<210> SEQ ID NO 190
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 190
gauagcauga auucugcau                                                  19

<210> SEQ ID NO 191
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 191
```
gcauacuagu acaaguggu                                              19

<210> SEQ ID NO 192
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 192
cugaagaugu accuauggu                                              19

<210> SEQ ID NO 193
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 193
caaaccuggu augaauaga                                              19

<210> SEQ ID NO 194
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 194
caagauacaa ucucacucu                                              19

<210> SEQ ID NO 195
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 195
gaauugcuau gugaaacua                                              19

<210> SEQ ID NO 196
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 196
gauuugaccu aaucacuaa                                              19

<210> SEQ ID NO 197
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 197
ccaauccauu agcgacagu                                              19

<210> SEQ ID NO 198
<211> LENGTH: 19
<212> TYPE: RNA

```
<213> ORGANISM: Artificial Sequence
<220> FEATURE:
<223> OTHER INFORMATION: synthesized nucleotide

<400> SEQUENCE: 198
cagagaaaga aauggccau                                                19

<210> SEQ ID NO 199
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 199
cuuggccuca uaaaccugu                                                19

<210> SEQ ID NO 200
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 200
cuaguucaca gacaaggaa                                                19

<210> SEQ ID NO 201
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 201
ccauuagcga caguaggau                                                19

<210> SEQ ID NO 202
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 202
ccuacaucuu auuccuca                                                 19

<210> SEQ ID NO 203
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 203
cuaugguccu aguaggaaa                                                19

<210> SEQ ID NO 204
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 204
cugaaagaau uccuuaggu                                                19
```

<210> SEQ ID NO 205
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 205
cuauguuaca ccaucuuca                                              19

<210> SEQ ID NO 206
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 206
gaauuccuua gguaaucua                                              19

<210> SEQ ID NO 207
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 207
cacuauagua uaccaguga                                              19

<210> SEQ ID NO 208
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 208
caucagcaaa gacaagaca                                              19

<210> SEQ ID NO 209
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 209
caagaggagu acagugcaa                                              19

<210> SEQ ID NO 210
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 210
ggaauacuuu auaagccau                                              19

<210> SEQ ID NO 211
<211> LENGTH: 19
<212> TYPE: RNA
<213> ORGANISM: Artificial Sequence
<220> FEATURE:

```
<223> OTHER INFORMATION: synthesized nucleotide

<400> SEQUENCE: 211
caugaauucu gcauugaga                                                    19

<210> SEQ ID NO 212
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 212
guuuccaauu ccacugucu                                                    19

<210> SEQ ID NO 213
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 213
cauguccuau aguuuguca                                                    19

<210> SEQ ID NO 214
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 214
gugaaaguau cacuggacu                                                    19

<210> SEQ ID NO 215
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 215
gaguuucaca gcauggacu                                                    19

<210> SEQ ID NO 216
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 216
guaacauguu uaccuggaa                                                    19

<210> SEQ ID NO 217
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 217
cugaacuagu ucacagaca                                                    19
```

```
<210> SEQ ID NO 218
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 218
cucaagagaa ucugacaga                                                    19

<210> SEQ ID NO 219
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 219
guaacaguaa uacauucca                                                    19

<210> SEQ ID NO 220
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 220
caauccauua gcgacagua                                                    19

<210> SEQ ID NO 221
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 221
gaaagauacu cacaugagu                                                    19

<210> SEQ ID NO 222
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 222
ccaaaugugu aauauucca                                                    19

<210> SEQ ID NO 223
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 223
guuugggaua augauaggu                                                    19

<210> SEQ ID NO 224
<211> LENGTH: 19
<212> TYPE: RNA
<213> ORGANISM: Artificial Sequence
<220> FEATURE:
<223> OTHER INFORMATION: synthesized nucleotide
```

```
<400> SEQUENCE: 224
caacaauaga ggauuccua                                                  19

<210> SEQ ID NO 225
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 225
caugaacugu acuacuccu                                                  19

<210> SEQ ID NO 226
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 226
gaaacauuga gggaacaca                                                  19

<210> SEQ ID NO 227
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 227
cucuuggaua uucucgaca                                                  19

<210> SEQ ID NO 228
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 228
gcauuaacau guuugugga                                                  19

<210> SEQ ID NO 229
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 229
cugaauauaa acuuguggu                                                  19

<210> SEQ ID NO 230
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 230
guaaaggcgu guuugcuua                                                  19

<210> SEQ ID NO 231
<211> LENGTH: 19
```

```
<212> TYPE: RNA
<213> ORGANISM: Artificial Sequence
<220> FEATURE:
<223> OTHER INFORMATION: synthesized nucleotide

<400> SEQUENCE: 231
cuuugaacau cucuuugcu                                                19

<210> SEQ ID NO 232
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 232
ccauacuuca ggaacugca                                                19

<210> SEQ ID NO 233
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 233
cuauacauua guucgagaa                                                19

<210> SEQ ID NO 234
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 234
cuucuaggca ucauguccu                                                19

<210> SEQ ID NO 235
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 235
gaauaccuaa gauuucugu                                                19

<210> SEQ ID NO 236
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 236
cauacuagua caaguggua                                                19

<210> SEQ ID NO 237
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 237
```
cauaggaauu uagaaccua                                              19

<210> SEQ ID NO 238
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 238
gaaacuauua uaaggccau                                              19

<210> SEQ ID NO 239
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 239
cuuagcaaga aguuaugga                                              19

<210> SEQ ID NO 240
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 240
cuucuguguu aauacugga                                              19

<210> SEQ ID NO 241
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 241
cuuaaggcau acuaguaca                                              19

<210> SEQ ID NO 242
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 242
ccuauaguuu gucaucccu                                              19

<210> SEQ ID NO 243
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 243
cuuugagcuu ucauagaga                                              19

<210> SEQ ID NO 244
<211> LENGTH: 19
<212> TYPE: RNA
<213> ORGANISM: Artificial Sequence

```
<220> FEATURE:
<223> OTHER INFORMATION: synthesized nucleotide

<400> SEQUENCE: 244
caaguaggca uucuaggcu                                                   19

<210> SEQ ID NO 245
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 245
caagagacau aaucccggu                                                   19

<210> SEQ ID NO 246
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 246
caauuccacu gucuugugu                                                   19

<210> SEQ ID NO 247
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 247
guuauagcuu auuaggugu                                                   19

<210> SEQ ID NO 248
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 248
gauauucaua uugacccaa                                                   19

<210> SEQ ID NO 249
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 249
cauagagagu uucacagca                                                   19

<210> SEQ ID NO 250
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 250
guaaucuaua acuaggacu                                                   19
```

<210> SEQ ID NO 251
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 251
gaacacaaau uuaugggcu                                               19

<210> SEQ ID NO 252
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 252
guuuauagga guaugugcu                                               19

<210> SEQ ID NO 253
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 253
cauaaaggga uuugaccua                                               19

<210> SEQ ID NO 254
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 254
cauaagauuu acugcugcu                                               19

<210> SEQ ID NO 255
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 255
cuuugguaua cgacccaga                                               19

<210> SEQ ID NO 256
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 256
guaaacugaa acaugcaca                                               19

<210> SEQ ID NO 257
<211> LENGTH: 19
<212> TYPE: RNA
<213> ORGANISM: Artificial Sequence
<220> FEATURE:
<223> OTHER INFORMATION: synthesized nucleotide

```
<400> SEQUENCE: 257
ggaaacuauu auaaggcca                                              19

<210> SEQ ID NO 258
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 258
caauugugaa uguuggugu                                              19

<210> SEQ ID NO 259
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 259
cuaagugcca guauuccca                                              19

<210> SEQ ID NO 260
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 260
cauuugaaga uauucacca                                              19

<210> SEQ ID NO 261
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 261
cuuauuuccu cagggcuca                                              19

<210> SEQ ID NO 262
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 262
caaauaaaca ggugccuga                                              19

<210> SEQ ID NO 263
<211> LENGTH: 19
<212> TYPE: RNA
<213> ORGANISM: Artificial Sequence
<220> FEATURE:
<223> OTHER INFORMATION: synthesized nucleotide

<400> SEQUENCE: 263
ggugacuuag guucuagau                                              19

<210> SEQ ID NO 264
<211> LENGTH: 66
```

```
<212> TYPE: DNA
<213> ORGANISM: Artificial Sequence
<220> FEATURE:
<223> OTHER INFORMATION: synthesized nucleotide

<400> SEQUENCE: 264
tgctgaattc ggtgacttag gttctagatg ttttggccac tgactgacat ctagaataag    60
tcacca                                                                66

<210> SEQ ID NO 265
<211> LENGTH: 66
<212> TYPE: DNA
<213> ORGANISM: Artificial Sequence
<220> FEATURE:
<223> OTHER INFORMATION: synthesized nucleotide

<400> SEQUENCE: 265
tgctgaattc ggugacuuag guucuagaug ttttggccac tgactgacat ctagaataag    60
tcacca                                                                66

<210> SEQ ID NO 266
<211> LENGTH: 65
<212> TYPE: DNA
<213> ORGANISM: Artificial Sequence
<220> FEATURE:
<223> OTHER INFORMATION: synthesized nucleotide

<400> SEQUENCE: 266
cctgaccggt ggtgacttat tctagatgtc agtcagtggc caaaacatct agaacctaag    60
tcacc                                                                 65

<210> SEQ ID NO 267
<211> LENGTH: 64
<212> TYPE: DNA
<213> ORGANISM: Artificial Sequence
<220> FEATURE:
<223> OTHER INFORMATION: synthesized nucleotide

<400> SEQUENCE: 267
tgctgaaatg tactgcgcgt ggagacgttt tggccactga ctgacgtctc cacgcagtac    60
attt                                                                  64

<210> SEQ ID NO 268
<211> LENGTH: 64
<212> TYPE: DNA
<213> ORGANISM: Artificial Sequence
<220> FEATURE:
<223> OTHER INFORMATION: synthesized nucleotide

<400> SEQUENCE: 268
cctgaaatgt actgcgtgga gacgtcagtc agtggccaaa acgtctccac gcgcagtaca    60
tttc                                                                  64
```